(12) United States Patent
Chiang et al.

(10) Patent No.: US 7,411,059 B2
(45) Date of Patent: Aug. 12, 2008

(54) PRODUCTION OF SYRINGYL LIGNIN IN GYMNOSPERMS

(75) Inventors: Vincent L. Chiang, Hancock, MI (US); Daniel T. Carraway, Bainbridge, GA (US); Richard H. Smeltzer, Tallahassee, FL (US)

(73) Assignee: Arborgen, LLC, Summerville, SC (US)

( * ) Notice: Subject to any disclaimer, the term of this patent is extended or adjusted under 35 U.S.C. 154(b) by 101 days.

(21) Appl. No.: 10/681,878

(22) Filed: Oct. 9, 2003

(65) Prior Publication Data

US 2005/0076403 A1 Apr. 7, 2005

Related U.S. Application Data

(60) Continuation of application No. 09/796,256, filed on Feb. 28, 2001, now abandoned, which is a division of application No. 08/991,677, filed on Dec. 16, 1997, now Pat. No. 6,252,135.

(60) Provisional application No. 60/033,381, filed on Dec. 16, 1996.

(51) Int. Cl.
C12N 15/29 (2006.01)
(52) U.S. Cl. .................................... 536/24.1
(58) Field of Classification Search ................ 536/24.1; 800/287, 278
See application file for complete search history.

(56) References Cited

U.S. PATENT DOCUMENTS

| | | | |
|---|---|---|---|
| 4,795,855 A | 1/1989 | Fillatti et al. |
| 4,801,545 A | 1/1989 | Stuart et al. |
| 4,886,937 A | 12/1989 | Sederoff et al. |
| 4,957,866 A | 9/1990 | Gupta et al. |
| 5,034,322 A | 7/1991 | Rogers et al. |
| 5,034,326 A | 7/1991 | Pullman et al. |
| 5,036,007 A | 7/1991 | Gupta et al. |
| 5,107,065 A | 4/1992 | Shewmaker |
| 5,122,466 A | 6/1992 | Stomp et al. |
| 5,187,092 A | 2/1993 | Uddin |
| 5,236,841 A | 8/1993 | Gupta et al. |
| 5,294,549 A | 3/1994 | Pullman et al. |
| 5,413,930 A | 5/1995 | Becwar et al. |
| 5,451,514 A | 9/1995 | Boudet et al. |
| 5,457,041 A | 10/1995 | Ginaven et al. |

OTHER PUBLICATIONS

Benfey et al (1990, Science 250:959-966).*
Benfey et al (1989, EMBO J, 8(8):2195-2202).*
Kojima et al (1994, The Plant Journal 6(4):591-596).*
Voo et al (1995 Plant Physiology 108:85-97).*
"cDNA cloning, sequence analysis and seasonal expression of lignin-bispecific caffeic acid/5-hydroxyferulic acid O-methyltransferase of aspen", by Robert C. Bugos, et al., Plant Molecular Biology 17: 1203-1215, 1991.
"Genetic engineering of wood", by Ross Whetten, et al., Forest Ecology and Management, 43 (1991) 301-316, Elsevier Science Publishers B. V., Amsterdam.
"Logger and Lumberman" from Trailer Director Portable Sawmills & Firewood Processors, Dec. 15, 1995.

* cited by examiner

*Primary Examiner*—Stuart F. Baum
(74) *Attorney, Agent, or Firm*—Foley & Lardner LLP

(57) ABSTRACT

The present invention relates to a method for producing syringyl lignin in gymnosperms. The production of syringyl lignin in gymnosperms is accomplished by genetically transforming a gymnosperm genome, which does not normally contain genes which code for enzymes necessary for production of syringyl lignin, with DNA which codes for enzymes found in angiosperms associated with production of syringyl lignin. The expression of the inserted DNA is mediated using host promoter regions in the gymnosperm. In addition, genetic sequences which code for gymnosperm lignin antisense mRNA may be incorporated into the gymnosperm genome in order to suppress the formation of the less preferred forms of lignin in the gymnosperm such as guaiacyl lignin.

1 Claim, 33 Drawing Sheets

SEQ ID 5

<400> 5

```
cggcacgagc cctacctcct ttcttggaaa aatttcccca ttcgatcaca atccgggcct    60
```

| caaaaa | atg | gga | tca | aca | agc | gaa | acg | aag | atg | agc | ccg | agt | gaa | gca | 108 |
|---|---|---|---|---|---|---|---|---|---|---|---|---|---|---|---|
| | Met | Gly | Ser | Thr | Ser | Glu | Thr | Lys | Met | Ser | Pro | Ser | Glu | Ala | |
| | 1 | | | | 5 | | | | | 10 | | | | | |

| gca | gca | gca | gaa | gaa | gaa | gca | ttc | gta | ttc | gct | atg | caa | tta | acc | agt | 156 |
|---|---|---|---|---|---|---|---|---|---|---|---|---|---|---|---|---|
| Ala | Ala | Ala | Glu | Glu | Glu | Ala | Phe | Val | Phe | Ala | Met | Gln | Leu | Thr | Ser | |
| 15 | | | | | 20 | | | | | 25 | | | | | 30 | |

| gct | tca | gtt | ctt | ccc | atg | gtc | cta | aaa | tca | gcc | ata | gag | ctc | gac | gtc | 204 |
|---|---|---|---|---|---|---|---|---|---|---|---|---|---|---|---|---|
| Ala | Ser | Val | Leu | Pro | Met | Val | Leu | Lys | Ser | Ala | Ile | Glu | Leu | Asp | Val | |
| | | | | 35 | | | | | 40 | | | | | 45 | | |

| tta | gaa | atc | atg | gct | aaa | gct | ggt | cca | ggt | gcg | cac | ata | tcc | aca | tct | 252 |
|---|---|---|---|---|---|---|---|---|---|---|---|---|---|---|---|---|
| Leu | Glu | Ile | Met | Ala | Lys | Ala | Gly | Pro | Gly | Ala | His | Ile | Ser | Thr | Ser | |
| | | | 50 | | | | | 55 | | | | | 60 | | | |

| gac | ata | gcc | tct | aag | ctg | ccc | aca | aag | aat | cca | gat | gca | gcc | gtc | atg | 300 |
|---|---|---|---|---|---|---|---|---|---|---|---|---|---|---|---|---|
| Asp | Ile | Ala | Ser | Lys | Leu | Pro | Thr | Lys | Asn | Pro | Asp | Ala | Ala | Val | Met | |
| | | 65 | | | | | 70 | | | | | 75 | | | | |

| ctt | gac | cgt | atg | ctc | cgc | ctc | ttg | gct | agc | tac | tct | gtt | cta | acg | tgc | 348 |
|---|---|---|---|---|---|---|---|---|---|---|---|---|---|---|---|---|
| Leu | Asp | Arg | Met | Leu | Arg | Leu | Leu | Ala | Ser | Tyr | Ser | Val | Leu | Thr | Cys | |
| | | 80 | | | | | 85 | | | | | 90 | | | | |

| tct | ctc | cgc | acc | ctc | cct | gac | ggc | aag | atc | gag | agg | ctt | tac | ggc | ctt | 396 |
|---|---|---|---|---|---|---|---|---|---|---|---|---|---|---|---|---|
| Ser | Leu | Arg | Thr | Leu | Pro | Asp | Gly | Lys | Ile | Glu | Arg | Leu | Tyr | Gly | Leu | |
| 95 | | | | | 100 | | | | | 105 | | | | | 110 | |

| gca | ccc | gtt | tgt | aaa | ttc | ttg | acc | aga | aac | gat | gat | gga | gtc | tcc | ata | 444 |
|---|---|---|---|---|---|---|---|---|---|---|---|---|---|---|---|---|
| Ala | Pro | Val | Cys | Lys | Phe | Leu | Thr | Arg | Asn | Asp | Asp | Gly | Val | Ser | Ile | |
| | | | 115 | | | | | 120 | | | | | 125 | | | |

| gcc | gct | ctg | tct | ctc | atg | aat | caa | gac | aag | gtc | ctc | atg | gag | agc | tgg | 492 |
|---|---|---|---|---|---|---|---|---|---|---|---|---|---|---|---|---|
| Ala | Ala | Leu | Ser | Leu | Met | Asn | Gln | Asp | Lys | Val | Leu | Met | Glu | Ser | Trp | |
| | | | 130 | | | | | 135 | | | | | 140 | | | |

| tac | cac | ttg | acc | gag | gca | gtt | ctt | gaa | ggt | gga | att | cca | ttt | aac | aag | 540 |
|---|---|---|---|---|---|---|---|---|---|---|---|---|---|---|---|---|
| Tyr | His | Leu | Thr | Glu | Ala | Val | Leu | Glu | Gly | Gly | Ile | Pro | Phe | Asn | Lys | |
| | | 145 | | | | | 150 | | | | | 155 | | | | |

Fig. 2A

```
gcc tat gga atg aca gca ttt gag tac cat ggc acc gat ccc aga ttc    588
Ala Tyr Gly Met Thr Ala Phe Glu Tyr His Gly Thr Asp Pro Arg Phe
    160                 165                 170 aac aca gtt ttc aac aat gga atg tcc aat cat tcg acc att acc atg    636
Asn Thr Val Phe Asn Asn Gly Met Ser Asn His Ser Thr Ile Thr Met
175                 180                 185                 190 aag aaa atc ctt gag act tac aaa ggg ttc gag gga ctt gga tct gtg    684
Lys Lys Ile Leu Glu Thr Tyr Lys Gly Phe Glu Gly Leu Gly Ser Val
                195                 200                 205 gtt gat gtt ggt ggt ggc act ggt gcc cac ctt aac atg att atc gct    732
Val Asp Val Gly Gly Gly Thr Gly Ala His Leu Asn Met Ile Ile Ala
                210                 215                 220 aaa tac ccc atg atc aag ggc att aac ttc gac ttg cct cat gtt att    780
Lys Tyr Pro Met Ile Lys Gly Ile Asn Phe Asp Leu Pro His Val Ile
            225                 230                 235 gag gag gct ccc tcc tat cct ggt gtg gag cat gtt ggt gga gat atg    828
Glu Glu Ala Pro Ser Tyr Pro Gly Val Glu His Val Gly Gly Asp Met
        240                 245                 250 ttt gtt agt gtt cca aaa gga gat gcc att ttc atg aag tgg ata tgt    876
Phe Val Ser Val Pro Lys Gly Asp Ala Ile Phe Met Lys Trp Ile Cys
255                 260                 265                 270 cat gat tgg agc gat gaa cac tgc ttg aag ttt ttg aag aaa tgt tat    924
His Asp Trp Ser Asp Glu His Cys Leu Lys Phe Leu Lys Lys Cys Tyr
                275                 280                 285 gaa gca ctt cca acc aat ggg aag gtg atc ctt gct gaa tgc atc ctc    972
Glu Ala Leu Pro Thr Asn Gly Lys Val Ile Leu Ala Glu Cys Ile Leu
                290                 295                 300 ccc gtg gcg cca gac gca agc ctc ccc act aag gca gtg gtc cat att   1020
Pro Val Ala Pro Asp Ala Ser Leu Pro Thr Lys Ala Val Val His Ile
            305                 310                 315 gat gtc atc atg ttg gct cat aac cca ggt ggg aaa gag aga act gag   1068
Asp Val Ile Met Leu Ala His Asn Pro Gly Gly Lys Glu Arg Thr Glu
        320                 325                 330 aag gag ttt gag gcc ttg gcc aag ggg gct gga ttt gaa ggt ttc cga   1116
Lys Glu Phe Glu Ala Leu Ala Lys Gly Ala Gly Phe Glu Gly Phe Arg
```

Fig. 2B

```
        335                 340                 345                 350
gta gta gcc tcg tgc gct tac aat aca tgg atc atc gaa ttt ttg aag    1164
Val Val Ala Ser Cys Ala Tyr Asn Thr Trp Ile Ile Glu Phe Leu Lys
                355                 360                 365 aag att tgagtcctta ctcggctttg agtacataat accaactcct tttggttttc    1220
Lys Ile gagattgtga ttgtgattgt gattgtctct ctttcgcagt tggccttatg atataatgta 1280
tcgttaactc gatcacagaa gtgcaaaaga cagtgaatgt acactgcttt ataaataaa  1340 aattttaaga ttttgattca tgtaaaaaaa aaaaaaaaa                         1380
```

| | | | | | | | | | | | | | | |
|---|---|---|---|---|---|---|---|---|---|---|---|---|---|---|
|Met|Gly|Ser|Thr|Ser|Glu|Thr|Lys|Met|Ser|Pro|Ser|Glu|Ala|Ala|Ala
|1| | | |5| | | | |10| | | | |15|

Ala Glu Glu Glu Ala Phe Val Phe Ala Met Gln Leu Thr Ser Ala Ser
 20 25 30

Val Leu Pro Met Val Leu Lys Ser Ala Ile Glu Leu Asp Val Leu Glu
 35 40 45

Ile Met Ala Lys Ala Gly Pro Gly Ala His Ile Ser Thr Ser Asp Ile
 50 55 60

Ala Ser Lys Leu Pro Thr Lys Asn Pro Asp Ala Ala Val Met Leu Asp
65 70 75 80

Arg Met Leu Arg Leu Leu Ala Ser Tyr Ser Val Leu Thr Cys Ser Leu
 85 90 95

Arg Thr Leu Pro Asp Gly Lys Ile Glu Arg Leu Tyr Gly Leu Ala Pro
 100 105 110

Val Cys Lys Phe Leu Thr Arg Asn Asp Asp Gly Val Ser Ile Ala Ala
 115 120 125

Leu Ser Leu Met Asn Gln Asp Lys Val Leu Met Glu Ser Trp Tyr His
 130 135 140

Leu Thr Glu Ala Val Leu Glu Gly Gly Ile Pro Phe Asn Lys Ala Tyr
145 150 155 160

Gly Met Thr Ala Phe Glu Tyr His Gly Thr Asp Pro Arg Phe Asn Thr
 165 170 175

Val Phe Asn Asn Gly Met Ser Asn His Ser Thr Ile Thr Met Lys Lys
 180 185 190

Ile Leu Glu Thr Tyr Lys Gly Phe Glu Gly Leu Gly Ser Val Val Asp
 195 200 205

Val Gly Gly Gly Thr Gly Ala His Leu Asn Met Ile Ile Ala Lys Tyr
 210 215 220

Pro Met Ile Lys Gly Ile Asn Phe Asp Leu Pro His Val Ile Glu Glu
225 230 235 240

Fig. 2D

```
Ala Pro Ser Tyr Pro Gly Val Glu His Val Gly Gly Asp Met Phe Val
                245                 250                 255

Ser Val Pro Lys Gly Asp Ala Ile Phe Met Lys Trp Ile Cys His Asp
            260                 265                 270

Trp Ser Asp Glu His Cys Leu Lys Phe Leu Lys Lys Cys Tyr Glu Ala
        275                 280                 285

Leu Pro Thr Asn Gly Lys Val Ile Leu Ala Glu Cys Ile Leu Pro Val
    290                 295                 300

Ala Pro Asp Ala Ser Leu Pro Thr Lys Ala Val Val His Ile Asp Val
305                 310                 315                 320

Ile Met Leu Ala His Asn Pro Gly Gly Lys Glu Arg Thr Glu Lys Glu
                325                 330                 335

Phe Glu Ala Leu Ala Lys Gly Ala Gly Phe Glu Gly Phe Arg Val Val
            340                 345                 350

Ala Ser Cys Ala Tyr Asn Thr Trp Ile Ile Glu Phe Leu Lys Lys Ile
        355                 360                 365
```

Fig. 2E

```
<400> 7
cggcacgagc tcattttcca cttctggttt gatctctgca attcttccat cagtcccta      59 atg gag acc caa aca aaa caa gaa gaa atc ata tat cgg tcg aaa ctc      107
Met Glu Thr Gln Thr Lys Gln Glu Glu Ile Ile Tyr Arg Ser Lys Leu
 1               5                  10                  15 ccc gat atc tac atc ccc aaa cac ctc cct tta cat tcg tat tgt ttc      155
Pro Asp Ile Tyr Ile Pro Lys His Leu Pro Leu His Ser Tyr Cys Phe
                20                  25                  30 gag aac atc tca cag ttc ggc tcc cgc ccc tgt ctg atc aat ggc gca      203
Glu Asn Ile Ser Gln Phe Gly Ser Arg Pro Cys Leu Ile Asn Gly Ala
            35                  40                  45 acg ggc aag tat tac aca tat gct gag gtt gag ctc att gcg cgc aag      251
Thr Gly Lys Tyr Tyr Thr Tyr Ala Glu Val Glu Leu Ile Ala Arg Lys
        50                  55                  60 gtc gca tcc ggc ctc aac aaa ctc ggc gtt cga caa ggt gac atc atc      299
Val Ala Ser Gly Leu Asn Lys Leu Gly Val Arg Gln Gly Asp Ile Ile
 65                  70                  75                  80 atg ctt ttg cta ccc aac tcg ccg gag ttc gtg ttt tca att ctc ggc      347
Met Leu Leu Leu Pro Asn Ser Pro Glu Phe Val Phe Ser Ile Leu Gly
                85                  90                  95 gca tcc tac cgc ggg gct gcc gcc acc gcc gca aac ccg ttt tat acc      395
Ala Ser Tyr Arg Gly Ala Ala Ala Thr Ala Ala Asn Pro Phe Tyr Thr
            100                 105                 110 cct gcc gag atc agg aag caa gcc aaa acc tcc aac gcc agg ctt att      443
Pro Ala Glu Ile Arg Lys Gln Ala Lys Thr Ser Asn Ala Arg Leu Ile
        115                 120                 125 atc aca cat gcc tgt tac tat gag aaa gtg aag gac ttg gtg gaa gag      491
Ile Thr His Ala Cys Tyr Tyr Glu Lys Val Lys Asp Leu Val Glu Glu
130                 135                 140 aac gtt gcc aag atc ata tgt ata gac tca ccc ccg gac ggt tgt ttg      539
Asn Val Ala Lys Ile Ile Cys Ile Asp Ser Pro Pro Asp Gly Cys Leu
145                 150                 155                 160
```

Fig. 3A

```
cac ttc tcg g..g ctg agt gag gcg gac gag aac gac atg ccc aat gta    587
His Phe Ser Glu Leu Ser Glu Ala Asp Glu Asn Asp Met Pro Asn Val
            165                 170                 175 gag att gac ccc gat gat gtg gtg gcg ctg ccg tac tcg tca ggg acg    635
Glu Ile Asp Pro Asp Asp Val Val Ala Leu Pro Tyr Ser Ser Gly Thr
            180                 185                 190 acg ggt tta cca aag ggg gtg atg cta aca cac aag gga caa gtg acg    683
Thr Gly Leu Pro Lys Gly Val Met Leu Thr His Lys Gly Gln Val Thr
            195                 200                 205 agt gtg gcg caa cag gtg gac gga gag aat ccg aac ctg tat ata cat    731
Ser Val Ala Gln Gln Val Asp Gly Glu Asn Pro Asn Leu Tyr Ile His
            210                 215                 220 agc gag gac gtg gtt ctg tgc gtg ttg cct ctg ttt cac atc tac tcg    779
Ser Glu Asp Val Val Leu Cys Val Leu Pro Leu Phe His Ile Tyr Ser
225                 230                 235                 240 atg aac gtc atg ttt tgc ggg tta cga gtt ggt gcg gcg att ctg att    827
Met Asn Val Met Phe Cys Gly Leu Arg Val Gly Ala Ala Ile Leu Ile
                245                 250                 255 atg cag aaa ttt gaa ata tat ggg ttg tta gag ctg gtc aga agt aca    875
Met Gln Lys Phe Glu Ile Tyr Gly Leu Leu Glu Leu Val Arg Ser Thr
            260                 265                 270 ggt gac cat cat gcc tat cgt aca ccc atc gta ttg gca atc tcc aag    923
Gly Asp His His Ala Tyr Arg Thr Pro Ile Val Leu Ala Ile Ser Lys
            275                 280                 285 act ccg gat ctt cac aac tat gat gtg tcc tcc att cgg act gtc atg    971
Thr Pro Asp Leu His Asn Tyr Asp Val Ser Ser Ile Arg Thr Val Met
            290                 295                 300 tca ggt gcg gct cct ctg ggc aag gaa ctt gaa gat tct gtc aga gct    1019
Ser Gly Ala Ala Pro Leu Gly Lys Glu Leu Glu Asp Ser Val Arg Ala
305                 310                 315                 320 aag ttt ccc acc gcc aaa ctt ggt cag gga tat gga atg acg gag gca    1067
Lys Phe Pro Thr Ala Lys Leu Gly Gln Gly Tyr Gly Met Thr Glu Ala
                325                 330                 335 ggg ccc gtg cta gcg atg tgt ttg gca ttt gcc aag gaa ggg ttt gaa    1115
Gly Pro Val Leu Ala Met Cys Leu Ala Phe Ala Lys Glu Gly Phe Glu
            340                 345                 350
```

Fig. 3B

| | | | | | | | | | | | | | | |
|---|---|---|---|---|---|---|---|---|---|---|---|---|---|---|
| ata | aaa | tcg | ggg | gca | tct | gga | act | gtt | tta | agg | aac | gca | cag | atg | aag | 1163 |
| Ile | Lys | Ser | Gly | Ala | Ser | Gly | Thr | Val | Leu | Arg | Asn | Ala | Gln | Met | Lys | |
| | | 355 | | | | 360 | | | | | 365 | | | | | | att gtg gac cct gaa acc ggt gtc act ctc cct cga aac caa ccc gga 1211
Ile Val Asp Pro Glu Thr Gly Val Thr Leu Pro Arg Asn Gln Pro Gly
        370             375             380 gag att tgc att aga gga gac caa atc atg aaa ggt tat ctt aat gat 1259
Glu Ile Cys Ile Arg Gly Asp Gln Ile Met Lys Gly Tyr Leu Asn Asp
385             390             395             400 cct gag gcg acg gag aga acc ata gac aag gaa ggt tgg tta cac aca 1307
Pro Glu Ala Thr Glu Arg Thr Ile Asp Lys Glu Gly Trp Leu His Thr
                405             410             415 ggt gat gtg ggc tac atc gac gat gac act gag ctc ttc att gtt gat 1355
Gly Asp Val Gly Tyr Ile Asp Asp Asp Thr Glu Leu Phe Ile Val Asp
            420             425             430 cgg ttg aag gaa ctg atc aaa tac aaa ggg ttt cag gtg gca ccc gct 1403
Arg Leu Lys Glu Leu Ile Lys Tyr Lys Gly Phe Gln Val Ala Pro Ala
        435             440             445 gag ctt gag gcc atg ctc ctc aac cat ccc aac atc tct gat gct gcc 1451
Glu Leu Glu Ala Met Leu Leu Asn His Pro Asn Ile Ser Asp Ala Ala
    450             455             460 gtc gtc cca atg aaa gac gat gaa gct gga gag ctc cct gtg gcg ttt 1499
Val Val Pro Met Lys Asp Asp Glu Ala Gly Glu Leu Pro Val Ala Phe
465             470             475             480 gtt gta aga tca gat ggt tct cag ata tcc gag gct gaa atc agg caa 1547
Val Val Arg Ser Asp Gly Ser Gln Ile Ser Glu Ala Glu Ile Arg Gln
            485             490             495 tac atc gca aaa cag gtg gtt ttt tat aaa aga ata cat cgc gta ttt 1595
Tyr Ile Ala Lys Gln Val Val Phe Tyr Lys Arg Ile His Arg Val Phe
        500             505             510 ttc gtc gaa gcc att cct aaa gcg ccc tct ggc aaa atc ttg cgg aag 1643
Phe Val Glu Ala Ile Pro Lys Ala Pro Ser Gly Lys Ile Leu Arg Lys
    515             520             525 gac ctg aga gcc aaa ttg gcg tct ggt ctt ccc aat taattctcat 1689
Asp Leu Arg Ala Lys Leu Ala Ser Gly Leu Pro Asn
530             535             540

Fig. 3C

```
tcgctaccct cctttctctt atcatacgcc aacacgaacg aagaggctca attaaacgct 1749 gctcattcga agcggctcaa ttaaagctgc tcattcatgt ccaccgagtg ggcagcctgt 1809 cttgttggga tgttctttca tttgattcag ctgtgagaag ccagaccctc attatttatt 1869 gtgaaattca caagaatgtc tgtaaatcga tgttgtgagt gatgggtttc aaaacacttt 1929 tgacattgtt tacgttgtat ttcctgctgt tgaaaataac tactttgtat gacttttatt 1989 tgggaagata acctttcaaa aaaaaaaaaa aaaaaa                             2025
```

| | | | | | | | | | | | | | | |
|---|---|---|---|---|---|---|---|---|---|---|---|---|---|---|
| Met | Glu | Thr | Gln | Thr | Lys | Gln | Glu | Glu | Ile | Ile | Tyr | Arg | Ser | Lys | Leu |
| 1 | | | | 5 | | | | | 10 | | | | | 15 |

| Pro | Asp | Ile | Tyr | Ile | Pro | Lys | His | Leu | Pro | Leu | His | Ser | Tyr | Cys | Phe |
| | | | 20 | | | | | 25 | | | | | 30 | | |

| Glu | Asn | Ile | Ser | Gln | Phe | Gly | Ser | Arg | Pro | Cys | Leu | Ile | Asn | Gly | Ala |
| | | | 35 | | | | | 40 | | | | | 45 | | |

| Thr | Gly | Lys | Tyr | Tyr | Thr | Tyr | Ala | Glu | Val | Glu | Leu | Ile | Ala | Arg | Lys |
| | | 50 | | | | | 55 | | | | | 60 | | | |

| Val | Ala | Ser | Gly | Leu | Asn | Lys | Leu | Gly | Val | Arg | Gln | Gly | Asp | Ile | Ile |
| 65 | | | | | 70 | | | | | 75 | | | | | 80 |

| Met | Leu | Leu | Leu | Pro | Asn | Ser | Pro | Glu | Phe | Val | Phe | Ser | Ile | Leu | Gly |
| | | | | 85 | | | | | 90 | | | | | 95 | |

| Ala | Ser | Tyr | Arg | Gly | Ala | Ala | Ala | Thr | Ala | Ala | Asn | Pro | Phe | Tyr | Thr |
| | | | 100 | | | | | 105 | | | | | 110 | | |

| Pro | Ala | Glu | Ile | Arg | Lys | Gln | Ala | Lys | Thr | Ser | Asn | Ala | Arg | Leu | Ile |
| | | | 115 | | | | | 120 | | | | | 125 | | |

| Ile | Thr | His | Ala | Cys | Tyr | Tyr | Glu | Lys | Val | Lys | Asp | Leu | Val | Glu | Glu |
| | | 130 | | | | | 135 | | | | | 140 | | | |

| Asn | Val | Ala | Lys | Ile | Ile | Cys | Ile | Asp | Ser | Pro | Pro | Asp | Gly | Cys | Leu |
| 145 | | | | | 150 | | | | | 155 | | | | | 160 |

| His | Phe | Ser | Glu | Leu | Ser | Glu | Ala | Asp | Glu | Asn | Asp | Met | Pro | Asn | Val |
| | | | | 165 | | | | | 170 | | | | | 175 | |

| Glu | Ile | Asp | Pro | Asp | Asp | Val | Val | Ala | Leu | Pro | Tyr | Ser | Ser | Gly | Thr |
| | | | 180 | | | | | 185 | | | | | 190 | | |

| Thr | Gly | Leu | Pro | Lys | Gly | Val | Met | Leu | Thr | His | Lys | Gly | Gln | Val | Thr |
| | | | 195 | | | | | 200 | | | | | 205 | | |

| Ser | Val | Ala | Gln | Gln | Val | Asp | Gly | Glu | Asn | Pro | Asn | Leu | Tyr | Ile | His |
| | | 210 | | | | | 215 | | | | | 220 | | | |

| Ser | Glu | Asp | Val | Val | Leu | Cys | Val | Leu | Pro | Leu | Phe | His | Ile | Tyr | Ser |
| 225 | | | | | 230 | | | | | 235 | | | | | 240 |

Fig. 3E

```
Met Asn Val Met Phe Cys Gly Leu Arg Val Gly Ala Ala Ile Leu Ile
            245                 250                 255

Met Gln Lys Phe Glu Ile Tyr Gly Leu Leu Glu Leu Val Arg Ser Thr
            260                 265                 270

Gly Asp His His Ala Tyr Arg Thr Pro Ile Val Leu Ala Ile Ser Lys
            275                 280                 285

Thr Pro Asp Leu His Asn Tyr Asp Val Ser Ser Ile Arg Thr Val Met
            290                 295                 300

Ser Gly Ala Ala Pro Leu Gly Lys Glu Leu Glu Asp Ser Val Arg Ala
305                 310                 315                 320

Lys Phe Pro Thr Ala Lys Leu Gly Gln Gly Tyr Gly Met Thr Glu Ala
            325                 330                 335

Gly Pro Val Leu Ala Met Cys Leu Ala Phe Ala Lys Glu Gly Phe Glu
            340                 345                 350

Ile Lys Ser Gly Ala Ser Gly Thr Val Leu Arg Asn Ala Gln Met Lys
            355                 360                 365

Ile Val Asp Pro Glu Thr Gly Val Thr Leu Pro Arg Asn Gln Pro Gly
            370                 375                 380

Glu Ile Cys Ile Arg Gly Asp Gln Ile Met Lys Gly Tyr Leu Asn Asp
385                 390                 395                 400

Pro Glu Ala Thr Glu Arg Thr Ile Asp Lys Glu Gly Trp Leu His Thr
            405                 410                 415

Gly Asp Val Gly Tyr Ile Asp Asp Thr Glu Leu Phe Ile Val Asp
            420                 425                 430

Arg Leu Lys Glu Leu Ile Lys Tyr Lys Gly Phe Gln Val Ala Pro Ala
            435                 440                 445

Glu Leu Glu Ala Met Leu Leu Asn His Pro Asn Ile Ser Asp Ala Ala
            450                 455                 460

Val Val Pro Met Lys Asp Asp Glu Ala Gly Glu Leu Pro Val Ala Phe
465                 470                 475                 480
```

Fig. 3F

```
Val Val Arg Ser Asp Gly Ser Gln Ile Ser Glu Ala Glu Ile Arg Gln
                485                 490                 495

Tyr Ile Ala Lys Gln Val Val Phe Tyr Lys Arg Ile His Arg Val Phe
            500                 505                 510

Phe Val Glu Ala Ile Pro Lys Ala Pro Ser Gly Lys Ile Leu Arg Lys
        515                 520                 525

Asp Leu Arg Ala Lys Leu Ala Ser Gly Leu Pro Asn
    530                 535                 540
```

Fig. 3G

```
           cggcacgagg aaaccctaaa actcacctct cttacccttt ctcttca atg gct ttc      56
                                                              Met Ala Phe
                                                              1 ctt cta ata ccc atc tca ata atc ttc atc gtc tta gct tac cag ctc              104
Leu Leu Ile Pro Ile Ser Ile Ile Phe Ile Val Leu Ala Tyr Gln Leu
        5               10              15 tat caa cgg ctc aga ttt aag ctc cca ccc ggc cca cgt cca tgg ccg              152
Tyr Gln Arg Leu Arg Phe Lys Leu Pro Pro Gly Pro Arg Pro Trp Pro
20              25              30              35 atc gtc gga aac ctt tac gac ata aaa ccg gtg agg ttc cgg tgt ttc              200
Ile Val Gly Asn Leu Tyr Asp Ile Lys Pro Val Arg Phe Arg Cys Phe
                40              45              50 gcc gag tgg tca caa gcg tac ggt ccg atc ata tcg gtg tgg ttc ggt              248
Ala Glu Trp Ser Gln Ala Tyr Gly Pro Ile Ile Ser Val Trp Phe Gly
            55              60              65 tca acg ttg aat gtg atc gta tcg aat tcg gaa ttg gct aag gaa gtg              296
Ser Thr Leu Asn Val Ile Val Ser Asn Ser Glu Leu Ala Lys Glu Val
                70              75              80 ctc aag gaa aaa gat caa caa ttg gct gat agg cat agg agt aga tca              344
Leu Lys Glu Lys Asp Gln Gln Leu Ala Asp Arg His Arg Ser Arg Ser
        85              90              95 gct gcc aaa ttt agc agg gat ggg cag gac ctt ata tgg gct gat tat              392
Ala Ala Lys Phe Ser Arg Asp Gly Gln Asp Leu Ile Trp Ala Asp Tyr
100             105             110             115 gga cct cac tat gtg aag gtt aca aag gtt tgt acc ctc gag ctt ttt              440
Gly Pro His Tyr Val Lys Val Thr Lys Val Cys Thr Leu Glu Leu Phe
                120             125             130 act cca aag cgg ctt gaa gct ctt aga ccc att aga gaa gat gaa gtt              488
Thr Pro Lys Arg Leu Glu Ala Leu Arg Pro Ile Arg Glu Asp Glu Val
            135             140             145 aca gcc atg gtt gag tcc att ttt aat gac act gcg aat cct gaa aat              536
Thr Ala Met Val Glu Ser Ile Phe Asn Asp Thr Ala Asn Pro Glu Asn
        150             155             160
```

Fig. 4A

```
tat ggg aag agt atg ctg gtg aag aag tat ttg gga gca gta gca ttc    584
Tyr Gly Lys Ser Met Leu Val Lys Lys Tyr Leu Gly Ala Val Ala Phe
    165                 170                 175 aac aac att aca aga ctc gca ttt gga aag cga ttc gtg aat tca gag    632
Asn Asn Ile Thr Arg Leu Ala Phe Gly Lys Arg Phe Val Asn Ser Glu
180                 185                 190                 195 ggt gta atg gac gag caa gga ctt gaa ttt aag gaa att gtg gcc aat    680
Gly Val Met Asp Glu Gln Gly Leu Glu Phe Lys Glu Ile Val Ala Asn
                    200                 205                 210 gga ctc aag ctt ggt gcc tca ctt gca atg gct gag cac att cct tgg    728
Gly Leu Lys Leu Gly Ala Ser Leu Ala Met Ala Glu His Ile Pro Trp
            215                 220                 225 ctc cgt tgg atg ttc cca ctt gag gaa ggg gcc ttt gcc aag cat ggg    776
Leu Arg Trp Met Phe Pro Leu Glu Glu Gly Ala Phe Ala Lys His Gly
        230                 235                 240 gca cgt agg gac cga ctt acc aga gct atc atg gaa gag cac aca ata    824
Ala Arg Arg Asp Arg Leu Thr Arg Ala Ile Met Glu Glu His Thr Ile
    245                 250                 255 gcc cgt aaa aag agt ggt gga gcc caa caa cat ttc gtg gat gca ttg    872
Ala Arg Lys Lys Ser Gly Gly Ala Gln Gln His Phe Val Asp Ala Leu
260                 265                 270                 275 ctc acc cta caa gag aaa tat gac ctt agc gag gac act att att ggg    920
Leu Thr Leu Gln Glu Lys Tyr Asp Leu Ser Glu Asp Thr Ile Ile Gly
                    280                 285                 290 ctc ctt tgg gat atg atc act gca ggc atg gac aca acc gca atc tct    968
Leu Leu Trp Asp Met Ile Thr Ala Gly Met Asp Thr Thr Ala Ile Ser
            295                 300                 305 gtc gaa tgg gcc atg gcc gag tta att aag aac cca agg gtg caa caa   1016
Val Glu Trp Ala Met Ala Glu Leu Ile Lys Asn Pro Arg Val Gln Gln
        310                 315                 320 aaa gct caa gag gag cta gac aat gta ctt ggg tcc gaa cgt gtc ctg   1064
Lys Ala Gln Glu Glu Leu Asp Asn Val Leu Gly Ser Glu Arg Val Leu
    325                 330                 335
```

Fig. 4B

```
acc gaa ttg gac ttc tca agc ctc cct tat cta caa tgt gta gcc aag    1112
Thr Glu Leu Asp Phe Ser Ser Leu Pro Tyr Leu Gln Cys Val Ala Lys
340             345                 350                 355 gag gca cta agg ctg cac cct cca aca cca cta atg ctc cct cat cgc    1160
Glu Ala Leu Arg Leu His Pro Pro Thr Pro Leu Met Leu Pro His Arg
                360                 365                 370 gcc aat gcc aac gtc aaa att ggt ggc tac gac atc cct aag gga tca    1208
Ala Asn Ala Asn Val Lys Ile Gly Gly Tyr Asp Ile Pro Lys Gly Ser
                375                 380                 385 aat gtt cat gta aat gtc tgg gcc gtg gct cgt gat cca gca gtg tgg    1256
Asn Val His Val Asn Val Trp Ala Val Ala Arg Asp Pro Ala Val Trp
                390                 395                 400 cgt gac cca cta gag ttt cga ccg gaa cgg ttc tct gaa gac gat gtc    1304
Arg Asp Pro Leu Glu Phe Arg Pro Glu Arg Phe Ser Glu Asp Asp Val
                405                 410                 415 gac atg aaa ggt cac gat tat agg cta ctg ccg ttt ggt gca ggg agg    1352
Asp Met Lys Gly His Asp Tyr Arg Leu Leu Pro Phe Gly Ala Gly Arg
420             425                 430                 435 cgt gtt tgc ccc ggt gca caa ctt ggc atc aat ttg gtc aca tcc atg    1400
Arg Val Cys Pro Gly Ala Gln Leu Gly Ile Asn Leu Val Thr Ser Met
                440                 445                 450 atg ggt cac cta ttg cac cat ttc tat tgg agc cct cct aaa ggt gta    1448
Met Gly His Leu Leu His His Phe Tyr Trp Ser Pro Pro Lys Gly Val
                455                 460                 465 aaa cca gag gag att gac atg tca gag aat cca gga ttg gtc acc tac    1496
Lys Pro Glu Glu Ile Asp Met Ser Glu Asn Pro Gly Leu Val Thr Tyr
                470                 475                 480 atg cga acc ccg gtg caa gct gtt ccc act cca agg ctg cct gct cac    1544
Met Arg Thr Pro Val Gln Ala Val Pro Thr Pro Arg Leu Pro Ala His
485             490                 495 ttg tac aaa cgt gta gct gtg gat atg taattcttag tttgttatta          1591
Leu Tyr Lys Arg Val Ala Val Asp Met
500             505
```

Fig. 4C

```
ttcatgctct taaggttttg gactttgaac ttatgatgag atttgtaaaa ttccaagtga 1651 tcaaatgaag aaaagaccaa ataaaaaggc ttgacgattt aaaaaaaaaa aaaaaa    1708
```

Fig. 4D

```
Met Ala Phe Leu Leu Ile Pro Ile Ser Ile Ile Phe Ile Val Leu Ala
 1               5                  10                 15

Tyr Gln Leu Tyr Gln Arg Leu Arg Phe Lys Leu Pro Pro Gly Pro Arg
             20                  25                 30

Pro Trp Pro Ile Val Gly Asn Leu Tyr Asp Ile Lys Pro Val Arg Phe
             35                  40                 45

Arg Cys Phe Ala Glu Trp Ser Gln Ala Tyr Gly Pro Ile Ile Ser Val
     50                  55                  60

Trp Phe Gly Ser Thr Leu Asn Val Ile Val Ser Asn Ser Glu Leu Ala
 65              70                  75                     80

Lys Glu Val Leu Lys Glu Lys Asp Gln Gln Leu Ala Asp Arg His Arg
             85                  90                 95

Ser Arg Ser Ala Ala Lys Phe Ser Arg Asp Gly Gln Asp Leu Ile Trp
             100                 105                110

Ala Asp Tyr Gly Pro His Tyr Val Lys Val Thr Lys Val Cys Thr Leu
             115                 120                125

Glu Leu Phe Thr Pro Lys Arg Leu Glu Ala Leu Arg Pro Ile Arg Glu
     130                 135                 140

Asp Glu Val Thr Ala Met Val Glu Ser Ile Phe Asn Asp Thr Ala Asn
145                 150                 155                160

Pro Glu Asn Tyr Gly Lys Ser Met Leu Val Lys Lys Tyr Leu Gly Ala
             165                 170                 175

Val Ala Phe Asn Asn Ile Thr Arg Leu Ala Phe Gly Lys Arg Phe Val
             180                 185                 190

Asn Ser Glu Gly Val Met Asp Glu Gln Gly Leu Glu Phe Lys Glu Ile
             195                 200                 205

Val Ala Asn Gly Leu Lys Leu Gly Ala Ser Leu Ala Met Ala Glu His
             210                 215                 220

Ile Pro Trp Leu Arg Trp Met Phe Pro Leu Glu Glu Gly Ala Phe Ala
225                 230                 235                 240
```

Fig. 4E

```
Lys His Gly Ala Arg Arg Asp Arg Leu Thr Arg Ala Ile Met Glu Glu
                245                 250                 255

His Thr Ile Ala Arg Lys Lys Ser Gly Gly Ala Gln Gln His Phe Val
                260                 265             270

Asp Ala Leu Leu Thr Leu Gln Glu Lys Tyr Asp Leu Ser Glu Asp Thr
            275                 280                 285

Ile Ile Gly Leu Leu Trp Asp Met Ile Thr Ala Gly Met Asp Thr Thr
        290                 295                 300

Ala Ile Ser Val Glu Trp Ala Met Ala Glu Leu Ile Lys Asn Pro Arg
305                 310                 315                 320

Val Gln Gln Lys Ala Gln Glu Glu Leu Asp Asn Val Leu Gly Ser Glu
                325                 330                 335

Arg Val Leu Thr Glu Leu Asp Phe Ser Ser Leu Pro Tyr Leu Gln Cys
            340                 345                 350

Val Ala Lys Glu Ala Leu Arg Leu His Pro Pro Thr Pro Leu Met Leu
            355                 360                 365

Pro His Arg Ala Asn Ala Asn Val Lys Ile Gly Gly Tyr Asp Ile Pro
    370                 375                 380

Lys Gly Ser Asn Val His Val Asn Val Trp Ala Val Ala Arg Asp Pro
385                 390                 395                 400

Ala Val Trp Arg Asp Pro Leu Glu Phe Arg Pro Glu Arg Phe Ser Glu
                405                 410                 415

Asp Asp Val Asp Met Lys Gly His Asp Tyr Arg Leu Leu Pro Phe Gly
                420                 425                 430

Ala Gly Arg Arg Val Cys Pro Gly Ala Gln Leu Gly Ile Asn Leu Val
            435                 440                 445

Thr Ser Met Met Gly His Leu Leu His His Phe Tyr Trp Ser Pro Pro
    450                 455                 460

Lys Gly Val Lys Pro Glu Glu Ile Asp Met Ser Glu Asn Pro Gly Leu
465                 470                 475                 480
```

Fig. 4F

```
Val Thr Tyr Met Arg Thr Pro Val Gln Ala Val Pro Thr Pro Arg Leu
                485                 490                 495

Pro Ala His Leu Tyr Lys Arg Val Ala Val Asp Met
            500                 505
```

Fig. 4G

<400> 3
```
tgcaaacctg cacaaacaaa gagagagaag aagaaaaagg aagagaggag agagagagag    60
agagagagaa gcc atg gat tct tct ctt cat gaa gcc ttg caa cca cta      109
               Met Asp Ser Ser Leu His Glu Ala Leu Gln Pro Leu
               1               5                   10 ccc atg acg ctg ttc ttc att ata cct ttg cta ctc tta ttg ggc cta     157
Pro Met Thr Leu Phe Phe Ile Ile Pro Leu Leu Leu Leu Leu Gly Leu
            15                  20                  25 gta tct cgg ctt cgc cag aga cta cca tac cca cca ggc cca aaa ggc     205
Val Ser Arg Leu Arg Gln Arg Leu Pro Tyr Pro Pro Gly Pro Lys Gly
        30                  35                  40 tta ccg gtg atc gga aac atg ctc atg atg gat caa ctc act cac cga     253
Leu Pro Val Ile Gly Asn Met Leu Met Met Asp Gln Leu Thr His Arg
45                  50                  55                  60 gga ctc gcc aaa ctc gcc aaa caa tac gg· ggt cta ttc cac ctc aag     301
Gly Leu Ala Lys Leu Ala Lys Gln Tyr Gly Gly Leu Phe His Leu Lys
                    65                  70                  75 atg gga ttc tta cac atg gtg gcc gtt tcc aca ccc gac atg gct cgc     349
Met Gly Phe Leu His Met Val Ala Val Ser Thr Pro Asp Met Ala Arg
                80                  85                  90 caa gtc ctt caa gtc caa gac aac atc ttc tcg aac cgg cca gcc acc     397
Gln Val Leu Gln Val Gln Asp Asn Ile Phe Ser Asn Arg Pro Ala Thr
            95                  100                 105 ata gcc atc agc tac ctc acc tat gac cga gcc gac atg gcc ttc gct     445
Ile Ala Ile Ser Tyr Leu Thr Tyr Asp Arg Ala Asp Met Ala Phe Ala
        110                 115                 120 cac tac ggc ccg ttt tgg cgt cag atg cgt aaa ctc tgc gtc atg aaa     493
His Tyr Gly Pro Phe Trp Arg Gln Met Arg Lys Leu Cys Val Met Lys
125                 130                 135                 140 tta ttt agc cgg aaa cga gcc gag tcg tgg gag tcg gtc cga gac gag     541
Leu Phe Ser Arg Lys Arg Ala Glu Ser Trp Glu Ser Val Arg Asp Glu
                    145                 150                 155 gtc gac tcg gca gta cga gtg gtc gcg tcc aat att ggg tcg acg gtg     589
Val Asp Ser Ala Val Arg Val Val Ala Ser Asn Ile Gly Ser Thr Val
                160                 165                 170
```

Fig. 5A

```
aat atc ggc gag ctg gtt ttt gct ctg acg aag aat att act tac agg    637
Asn Ile Gly Glu Leu Val Phe Ala Leu Thr Lys Asn Ile Thr Tyr Arg
        175                 180                 185 gcg gct ttt ggg acg atc tcg cat gag gac cag gac gag ttc gtg gcc    685
Ala Ala Phe Gly Thr Ile Ser His Glu Asp Gln Asp Glu Phe Val Ala
        190                 195                 200 ata ctg caa gag ttt tcg cag ctg ttt ggt gct ttt aat ata gct gat    733
Ile Leu Gln Glu Phe Ser Gln Leu Phe Gly Ala Phe Asn Ile Ala Asp
205                 210                 215                 220 ttt atc cct tgg ctc aaa tgg gtt cct cag ggg att aac gtc agg ctc    781
Phe Ile Pro Trp Leu Lys Trp Val Pro Gln Gly Ile Asn Val Arg Leu
                225                 230                 235 aac aag gca cga ggg gcg ctt gat ggg ttt att gac aag atc atc gac    829
Asn Lys Ala Arg Gly Ala Leu Asp Gly Phe Ile Asp Lys Ile Ile Asp
        240                 245                 250 gat cat ata cag aag ggg agt aaa aac tcg gag gag gtt gat act gat    877
Asp His Ile Gln Lys Gly Ser Lys Asn Ser Glu Glu Val Asp Thr Asp
        255                 260                 265 atg gta gat gat tta ctt gct ttt tac ggt gag gaa gcc aaa gta agc    925
Met Val Asp Asp Leu Leu Ala Phe Tyr Gly Glu Glu Ala Lys Val Ser
        270                 275                 280 gaa tct gac gat ctt caa aat tcc atc aaa ctc acc aaa gac aac atc    973
Glu Ser Asp Asp Leu Gln Asn Ser Ile Lys Leu Thr Lys Asp Asn Ile
285                 290                 295                 300 aaa gct atc atg gac gta atg ttt gga ggg acc gaa acg gtg gcg tcc    1021
Lys Ala Ile Met Asp Val Met Phe Gly Gly Thr Glu Thr Val Ala Ser
                305                 310                 315 gcg att gaa tgg gcc atg acg gag ctg atg aaa agc cca gaa gat cta    1069
Ala Ile Glu Trp Ala Met Thr Glu Leu Met Lys Ser Pro Glu Asp Leu
                320                 325                 330 aag aag gtc caa caa gaa ctc gcc gtg gtg gtg ggt ctt gac cgg cga    1117
Lys Lys Val Gln Gln Glu Leu Ala Val Val Val Gly Leu Asp Arg Arg
        335                 340                 345
```

Fig. 5B

```
gtc gaa gag aaa gac ttc gag aag ctc acc tac ttg aaa tgc gta ctg    1165
Val Glu Glu Lys Asp Phe Glu Lys Leu Thr Tyr Leu Lys Cys Val Leu
350                 355                 360 aag gaa gtc ctt cgc ctc cac cca ccc atc cca ctc ctc ctc cac gag    1213
Lys Glu Val Leu Arg Leu His Pro Pro Ile Pro Leu Leu Leu His Glu
365                 370                 375                 380 act gcc gag gac gcc gag gtc ggc ggc tac tac att ccg gcg aaa tcg    1261
Thr Ala Glu Asp Ala Glu Val Gly Gly Tyr Tyr Ile Pro Ala Lys Ser
                385                 390                 395 cgg gtg atg atc aac gcg tgc gcc atc ggc cgg gac aag aac tcg tgg    1309
Arg Val Met Ile Asn Ala Cys Ala Ile Gly Arg Asp Lys Asn Ser Trp
            400                 405                 410 gcc gac cca gat acg ttt agg ccc tcc agg ttt ctc aaa gac ggt gtg    1357
Ala Asp Pro Asp Thr Phe Arg Pro Ser Arg Phe Leu Lys Asp Gly Val
        415                 420                 425 ccc gat ttc aaa ggg aac aac ttc gag ttc atc cca ttc ggg tca ggt    1405
Pro Asp Phe Lys Gly Asn Asn Phe Glu Phe Ile Pro Phe Gly Ser Gly
    430                 435                 440 cgt cgg tct tgc ccc ggt atg caa ctc gga ctc tac gcg cta gag acg    1453
Arg Arg Ser Cys Pro Gly Met Gln Leu Gly Leu Tyr Ala Leu Glu Thr
445                 450                 455                 460 act gtg gct cac ctc ctt cac tgt ttc acg tgg gag ttg ccg gac ggg    1501
Thr Val Ala His Leu Leu His Cys Phe Thr Trp Glu Leu Pro Asp Gly
                465                 470                 475 atg aaa ccg agt gaa ctc gag atg aat gat gtg ttt gga ctc acc gcg    1549
Met Lys Pro Ser Glu Leu Glu Met Asn Asp Val Phe Gly Leu Thr Ala
            480                 485                 490 cca aga gcg att cga ctc acc gcc gtg ccg agt cca cgc ctt ctc tgt    1597
Pro Arg Ala Ile Arg Leu Thr Ala Val Pro Ser Pro Arg Leu Leu Cys
        495                 500                 505 cct ctc tat tgatcgaatg attggggag ctttgtggag gggcttttat             1646
Pro Leu Tyr
    510
```

Fig. 5C

```
ggagactcta tatatagatg ggaagtgaaa caacgacagg tgaatgcttg gattttggt   1706 atatattggg gagggagggg aaaaaaaaaa taatgaaagg aaagaaaaga gagaatttga  1766
atttctcttc ctctgtggat aaaagcctcg tttttaattg tttttatgtg gagatatttg  1826
tgtttgttta tttttatctc ttttttgca ataacactca aaataaaaa aaaaaa       1883
```

| | | | | | | | | | | | | | | |
|---|---|---|---|---|---|---|---|---|---|---|---|---|---|---|
| Met | Asp | Ser | Ser | Leu | His | Glu | Ala | Leu | Gln | Pro | Leu | Pro | Met | Thr | Leu |
| 1 | | | | 5 | | | | | 10 | | | | | 15 | |
| Phe | Phe | Ile | Ile | Pro | Leu | Leu | Leu | Leu | Leu | Gly | Leu | Val | Ser | Arg | Leu |
| | | | 20 | | | | | 25 | | | | | 30 | | |
| Arg | Gln | Arg | Leu | Pro | Tyr | Pro | Pro | Gly | Pro | Lys | Gly | Leu | Pro | Val | Ile |
| | | 35 | | | | | 40 | | | | | 45 | | | |
| Gly | Asn | Met | Leu | Met | Met | Asp | Gln | Leu | Thr | His | Arg | Gly | Leu | Ala | Lys |
| | 50 | | | | | 55 | | | | | 60 | | | | |
| Leu | Ala | Lys | Gln | Tyr | Gly | Gly | Leu | Phe | His | Leu | Lys | Met | Gly | Phe | Leu |
| 65 | | | | | 70 | | | | | 75 | | | | | 80 |
| His | Met | Val | Ala | Val | Ser | Thr | Pro | Asp | Met | Ala | Arg | Gln | Val | Leu | Gln |
| | | | | 85 | | | | | 90 | | | | | 95 | |
| Val | Gln | Asp | Asn | Ile | Phe | Ser | Asn | Arg | Pro | Ala | Thr | Ile | Ala | Ile | Ser |
| | | | 100 | | | | | 105 | | | | | 110 | | |
| Tyr | Leu | Thr | Tyr | Asp | Arg | Ala | Asp | Met | Ala | Phe | Ala | His | Tyr | Gly | Pro |
| | | 115 | | | | | 120 | | | | | 125 | | | |
| Phe | Trp | Arg | Gln | Met | Arg | Lys | Leu | Cys | Val | Met | Lys | Leu | Phe | Ser | Arg |
| | 130 | | | | | 135 | | | | | 140 | | | | |
| Lys | Arg | Ala | Glu | Ser | Trp | Glu | Ser | Val | Arg | Asp | Glu | Val | Asp | Ser | Ala |
| 145 | | | | | 150 | | | | | 155 | | | | | 160 |
| Val | Arg | Val | Val | Ala | Ser | Asn | Ile | Gly | Ser | Thr | Val | Asn | Ile | Gly | Glu |
| | | | | 165 | | | | | 170 | | | | | 175 | |
| Leu | Val | Phe | Ala | Leu | Thr | Lys | Asn | Ile | Thr | Tyr | Arg | Ala | Ala | Phe | Gly |
| | | | 180 | | | | | 185 | | | | | 190 | | |
| Thr | Ile | Ser | His | Glu | Asp | Gln | Asp | Glu | Phe | Val | Ala | Ile | Leu | Gln | Glu |
| | | 195 | | | | | 200 | | | | | 205 | | | |
| Phe | Ser | Gln | Leu | Phe | Gly | Ala | Phe | Asn | Ile | Ala | Asp | Phe | Ile | Pro | Trp |
| | 210 | | | | | 215 | | | | | 220 | | | | |
| Leu | Lys | Trp | Val | Pro | Gln | Gly | Ile | Asn | Val | Arg | Leu | Asn | Lys | Ala | Arg |
| 225 | | | | | 230 | | | | | 235 | | | | | 240 |

Fig. 5E

```
Gly Ala Leu Asp Gly Phe Ile Asp Lys Ile Ile Asp Asp His Ile Gln
                245                 250                 255

Lys Gly Ser Lys Asn Ser Glu Glu Val Asp Thr Asp Met Val Asp Asp
            260                 265                 270

Leu Leu Ala Phe Tyr Gly Glu Glu Ala Lys Val Ser Glu Ser Asp Asp
        275                 280                 285

Leu Gln Asn Ser Ile Lys Leu Thr Lys Asp Asn Ile Lys Ala Ile Met
    290                 295                 300

Asp Val Met Phe Gly Gly Thr Glu Thr Val Ala Ser Ala Ile Glu Trp
305                 310                 315                 320

Ala Met Thr Glu Leu Met Lys Ser Pro Glu Asp Leu Lys Lys Val Gln
                325                 330                 335

Gln Glu Leu Ala Val Val Val Gly Leu Asp Arg Arg Val Glu Glu Lys
            340                 345                 350

Asp Phe Glu Lys Leu Thr Tyr Leu Lys Cys Val Leu Lys Glu Val Leu
        355                 360                 365

Arg Leu His Pro Pro Ile Pro Leu Leu Leu His Glu Thr Ala Glu Asp
    370                 375                 380

Ala Glu Val Gly Gly Tyr Tyr Ile Pro Ala Lys Ser Arg Val Met Ile
385                 390                 395                 400

Asn Ala Cys Ala Ile Gly Arg Asp Lys Asn Ser Trp Ala Asp Pro Asp
                405                 410                 415

Thr Phe Arg Pro Ser Arg Phe Leu Lys Asp Gly Val Pro Asp Phe Lys
            420                 425                 430

Gly Asn Asn Phe Glu Phe Ile Pro Phe Gly Ser Gly Arg Arg Ser Cys
        435                 440                 445

Pro Gly Met Gln Leu Gly Leu Tyr Ala Leu Glu Thr Thr Val Ala His
    450                 455                 460

Leu Leu His Cys Phe Thr Trp Glu Leu Pro Asp Gly Met Lys Pro Ser
465                 470                 475                 480
```

Fig. 5F

Glu Leu Glu Met Asn Asp Val Phe Gly Leu Thr Ala Pro Arg Ala Ile
            485                 490                 495

Arg Leu Thr Ala Val Pro Ser Pro Arg Leu Leu Cys Pro Leu Tyr
            500                 505                 510

```
aaacaccaat ttaatgggat ttcagatttg tatcccatgc tattggctaa ggcatttttc   60
ttattgtaat ctaaccaatt ctaatttcca ccctggtgtg aactgactga caaatgcggt  120
ccgaaaacag cgaatgaaat gtctgggtga tcggtcaaac aagcggtggg cgagagagcg  180
cgggtgttgg cctagccggg atggggtag gtagacggcg tattaccggc gagttgtccg  240
aatggagttt tcggggtagg tagtaacgta gacgtcaatg gaaaaagtca taatctccgt  300
caaaaatcca accgctcctt cacatcgcag agttggtggc cacgggaccc tccacccact  360
cactcaatcg atcgcctgcc gtggttgccc attattcaac catacgccac ttgactcttc  420
accaacaatt ccaggccggc tttctataca atgtactgca caggaaaatc caatataaaa  480
agccggcctc tgcttccttc tcagtagccc ccagctcatt caattcttcc cactgcaggc  540
tacatttgtc agacacgttt tccgccattt ttcgcctgtt tctgcggaga atttgatcag  600
gttcggattg ggattgaatc aattgaaagg tttttatttt cagtatttcg atcgccatg   659
```

```
ggccgggtgg tgacatttat tcataaattc atctcaaaac aagaaggatt tacaaaaata   60
aagaaaaca  aaattttcat ctttaacata attataattg tgttcacaaa attcaaactt  120
aaacccttaa tataaagaat ttctttcaac aatacacttt aatcacaact tcttcaatca  180
caacctcgtc caacaaaatt aaaatagatt aataaataaa taaacttaac tatttaaaaa  240
aaatattat  acaaaattta ttaaaacttc aaaataaaca aacttttat  acaaaattca  300
tcaaaacttt aaaataaagc taaacactga aatgtgagt  acatttaaaa ggacgctgat  360
cacaaaaatt ttgaaaacat aaacaaactt gaaactctac cttttaagaa tgagtttgtc  420
gtctcattaa ctcattagtt ttatagttcg aatccaatta acgtatcttt tattttatgg  480
aataagggtg ttttaataag tgattttggg attttttag  taatttattt gtgatatgtt  540
atggagtttt taaaaatata tatatatata tatatttttg ggttgagttt acttaaaatt  600
tggaaaaggt tggtaagaac tataaattga gttgtgaatg agtgttttat ggatttttta  660
agatgttaaa tttatatatg taattaaaat tttattttga ataacaaaaa ttataattgg  720
ataaaaaatt gttttgttaa atttagagta aaaatttcaa aatctaaaat aattaaacac  780
tattattttt aaaaaatttg ttggtaaatt ttatcttata tttaagttaa aatttagaaa  840
aaattaattt taaattaata aacttttgaa gtcaaatatt ccaatatttt tccaaaatat  900
taaatctatt ttgcattcaa aatacaatttt aaataataaa acttcatgga atagattaac  960
caatttgtat aaaaaccaaa aatctcaaat aaaatttaaa ttacaaaaca ttatcaacat 1020
tatgatttca agaaagacaa taaccagttt ccaataaaat aaaaaacctc atggcccgta 1080
attaagatct cattaattaa ttcttatttt ttaatttttt tacatagaaa atatctttat 1140
attgtatcca agaaatatag aatgttctcg tccagggact attaatctcc aaacaagttt 1200
caaatcatt  acattaaagc tcatcatgtc atttgtggat tggaaattat attgtataag 1260
agaaatatag aatgttctcg tctagggact attaattcc  aaacaaattt caaatcatt  1320
```

Fig. 7A

```
acattaaagc tcatcatgtc atttgtggat tggaaattag acaaaaaaaa tcccaaatat 1380
ttctctcaat ctcccaaaat atagttcgaa ctccatattt ttggaaattg agaattttt  1440
tacccaataa tatatttttt tatacatttt agagattttc cagacatatt tgctctggga 1500
tttattggaa tgaaggttga gttataaact ttcagtaatc caagtatctt cggtttttga 1560
agatactaaa tccattatat aataaaaaca cattttaaac accaatttaa tgggatttca 1620
gatttgtatc ccatgctatt ggctaaggca tttttcttat tgtaatctaa ccaattctaa 1680
tttccaccct ggtgtgaact gactgacaaa tgcggtccga aaacagcgaa tgaaatgtct 1740
gggtgatcgg tcaancaagc ggtgggcgag agagcgcggg tgttggccta gccgggatgg 1800
gggtaggtag acggcgtatt accggcgagt tgtccgaatg gagttttcgg ggtaggtagt 1860
aacgtagacg tcaatggaaa aagtcataat ctccgtcaaa aatccaaccg ctccttcaca 1920
tcgcagagtt ggtggccacg ggaccctcca cccactcact cgatcgcctg ccgtggttgc 1980
ccattattca accatacgcc acttgactct tcaccaacaa ttccaggccg gctttctata 2040
caatgtactg cacaggaaaa tccaatataa aaagccggcc tctgcttcct tctcagtagc 2100
ccccagctca ttcaattctt cccactgcag gctacatttg tcagacacgt tttccgccat 2160
ttttcgcctg tttctgcgga gaatttgatc aggttcggat tgggattgaa tcaattgaaa 2220
ggttttatt ttcagtattt cgatcgccat g                                 2251
```

```
aaagataata tatgtgtatg cctactacta cacattgttt tgaagtgtgt aaacatagtg   60
caacactagg aggactcaca atgagcactt gttgacatga aactagctaa atgcccaaca  120
atattagtga aagctagtta aactaacccc tttgactttc aagatgatat atttatatcc  180
ctactacgtc ttcctctttt tgtctttctc ttgtgattaa accttccttg aaacaattct  240
caaatgtaaa attaaacctt gaaacttgta gagaccaaac ttccctagga gaaaccacat  300
ttatgacaac atatatacac caacccattg catactataa tattggaatt acctgcagcg  360
aacgaaagaa acgctgtctc accaactcgt gcactacatc ccgaaactta accttcccct  420
gatacagatt gaagagccga aaaagcgtg catccaaatt tctggtatgg tgaggagccg   480
aaaaacgcgt gcgcctaatt tttttgagat gggccggaaa ataatgcgtg catctaaatt  540
ttcacgtgtc gcgtattggc gaggttgcgc tgaatgtgat cctgtgcgtg agccacattc  600
attccattgg ttgacccgcc ggtaccgcga ggaccgtggg gtctcacaga tacgcggatg  660
gtggatcagc actgagaaga ttagatgatg accaggcggg catttgaagt aaaaacttgg  720
gggtggttgg caagtacgcg acaaagaggg gtagtgcgca aggaagcgag ttggatgcaa  780
ataatattac aaagtgggtt ggtgggcatg agcatcaacc agaatgatgt tgttgctggt  840
tccgtgcaaa ttctgaccag tagtttgaac aatactaccc aacttgtttt tggtaaaaca  900
tgaagtgggt aaggagaatt gaacttacgt ctcatggtaa agggcaaggg caaatgactt  960
aacacatacc tttaactaat aaaaataccc ctaacaaata cgaaaacgaa tgagttatca 1020
cagaccttca actaataaga tagccatcag acccacatct cctgactgac caaaaacaaa 1080
tgacttcaac caactaagat acccatcaaa gctaacccac aacccaattc ctcacttccc 1140
cttaccagac caaccaagca gacctacgcc attaactact ttaggacgtg ggaattgggg 1200
gtgccaccgt tgaagaatgg cactcagggt tggtaatccc tccacgtgta tgtagcagtc 1260
gtttggtgga gacggcgtgt ttgaatgtcc accttccagt ttggagaaca aggaaattgg 1320
```

Fig. 8A

```
gcttatatta ggcctggatc tcttgtttca gagcaggagt agttcaggac aggaactagc 1380
attcaagaat tcaattgccc tgccctgctc tgctctgctt tgctcaactt attgatccct 1440
gctctggttt gttcaatttc ttgacccctg ctgggttctg ctctggtttg cacactttct 1500
cgattatata agtcattttg gatccttgca aggaagagaa tatg              1544
```

Fig. 8B

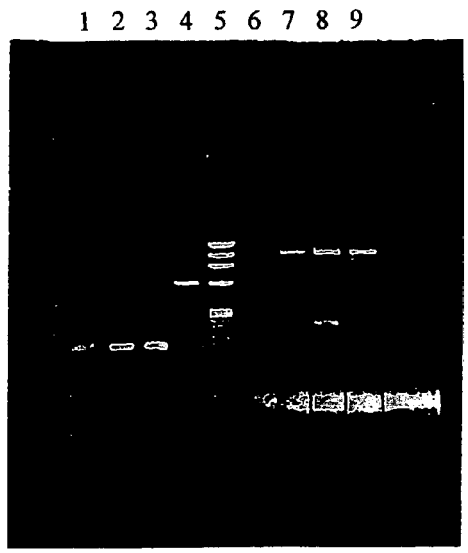

Lanes 1-4: PCT amplification of Sweetgum P450-1 gene from control and transgenic loblolly cell lines. Note the 600 bp amplified fragment in lanes 2-4.

Lanes 6-9: PCR amplification of Hygromycin gene from control and transgenic loblolly pine call lines. Note the 1000 bp amplified fragment in lanes 7-9.

Lane 1: Control PT52 line
Lane 2: Transgenic line Y2
Lane 3: Transgenic line Y17
Lane 4: Control plasmid pSSLsP450-1-im1-s
Lane 5: DNA size marker Phi 174/HaeII (BRL); top 4 bands indicate molecular size of 1354, 1078, 872 and 603 bp.
Lane 6: Control PT52 line
Lane 7: Transgenic line Y7
Lane 8: Transgenic line O4
Lane 9: Control plasmid pHygro

FIG. 9

PRODUCTION OF SYRINGYL LIGNIN IN GYMNOSPERMS

CROSS-REFERENCE TO RELATED APPLICATIONS

This application is a continuation of U.S. application Ser. No. 09/796,256, filed on Feb. 28, 2001 (now abandoned), which is a divisional of U.S. application Ser. No. 08/991,677, filed on Dec. 16, 1997 (now U.S. Pat. No. 6,252,135, issued on Jun. 26, 2001), claiming priority from Provisional Application No. 60/033,381, filed on Dec. 16, 1996.

FIELD OF THE INVENTION

The invention relates to the molecular modification of gymnosperms in order to cause the production of syringyl units during lignin biosynthesis and to production and propagation of gymnosperms containing syringyl lignin.

BACKGROUND OF THE INVENTION

Lignin is a major part of the supportive structure of most woody plants including angiosperm and gymnosperm trees which in turn are the principal sources of fiber for making paper and cellulosic products. In order to liberate fibers from wood structure in a manner suitable for making many grades of paper, it is necessary to remove much of the lignin from the fiber/lignin network. Lignin is removed from wood chips by treatment of the chips in an alkaline solution at elevated temperatures and pressure in an initial step of papermaking processes. The rate of removal of lignin from wood of different tree species varies depending upon lignin structure. Three different lignin structures have been identified in trees: p-hydroxyphenyl, guaiacyl and syringyl, which are illustrated in FIG. 1.

Angiosperm species, such as *Liquidambar styraciflua* L. [sweetgum], have lignin composed of a mixture of guaiacyl and syringyl monomer units. In contrast, gymnosperm species such as *Pinus taeda* L. [loblolly pine] have lignin which is devoid of syringyl monomer units. Generally speaking, the rate of delignification in a pulping process is directly proportional to the amount of syringyl lignin present in the wood. The higher delignification rates associated with species having a greater proportion of syringyl lignin result in more efficient pulp mill operations since the mills make better use of energy and capital investment and the environmental impact is lessened due to a decrease in chemicals used for delignification.

It is therefore an object of the invention to provide gymnosperm species which are easier to delignify in pulping processes.

Another object of the invention is to provide gymnosperm species such as loblolly pine which contain syringyl lignin.

An additional object of the invention is to provide a method for modifying genes involved in lignin biosynthesis in gymnosperm species so that production of syringyl lignin is increased while production of guaiacyl lignin is suppressed.

Still another object of the invention is to produce whole gymnosperm plants containing genes which increase production of syringyl lignin and repress production of guaiacyl lignin.

Yet another object of the invention is to identify, isolate and/or clone those genes in angiosperms responsible for production of syringyl lignin.

A further object of the invention is to provide, in gymnosperms, genes which produce syringyl lignin.

Another object of the invention is to provide a method for making an expression cassette insertable into a gymnosperm cell for the purpose of inducing formation of syringyl lignin in a gymnosperm plant derived from the cell.

DEFINITIONS

The term "promoter" refers to a DNA sequence in the 5' flanking region of a given gene which is involved in recognition and binding of RNA polymerase and other transcriptional proteins and is required to initiate DNA transcription in cells.

The term "constitutive promoter" refers to a promoter which activates transcription of a desired gene, and is commonly used in creation of an expression cassette designed for preliminary experiments relative to testing of gene function. An example of a constitutive promoter is 35S CaMV, available from Clonetech.

The term "expression cassette" refers to a double stranded DNA sequence which contains both promoters and genes such that expression of a given gene is achieved upon insertion of the expression cassette into a plant cell.

The term "plant" includes whole plants and portions of plants, including plant organs (e.g. roots, stems, leaves, etc.)

The term "angiosperm" refers to plants which produce seeds encased in an ovary. A specific example of an angiosperm is *Liquidambar styraciflua* (L.)[sweetgum]. The angiosperm sweetgum produces syringyl lignin.

The term "gymnosperm" refers to plants which produce naked seeds, that is, seeds which are not encased in an ovary. A specific example of a gymnosperm is *Pinus taeda* (L.) [loblolly pine]. The gymnosperm loblolly pine does not produce syringyl lignin.

SUMMARY OF THE INVENTION

With regard to the above and other objects, the invention provides a method for inducing production of syringyl lignin in gymnosperms and to gymnosperms which contain syringyl lignin for improved delignification in the production of pulp for papermaking and other applications. In accordance with one of its aspects, the invention involves cloning an angiosperm DNA sequence which codes for enzymes involved in production of syringyl lignin monomer units, fusing the angiosperm DNA sequence to a lignin promoter region to form an expression cassette, and inserting the expression cassette into a gymnosperm genome.

Enzymes required for production of syringyl lignin in an angiosperm are obtained by deducing an amino acid sequence of the enzyme, extrapolating an mRNA sequence from the amino acid sequence, constructing a probe for the corresponding DNA sequence and cloning the DNA sequence which codes for the desired enzyme. A promoter region specific to a gymnosperm lignin biosynthesis gene is identified by constructing a probe for a gymnosperm lignin biosynthesis gene, sequencing the 5' flanking region of the DNA which encodes the gymnosperm lignin biosynthesis gene to locate a promoter sequence, and then cloning that sequence.

An expression cassette is constructed by fusing the angiosperm syringyl lignin DNA sequence to the gymnosperm promoter DNA sequence. Alternatively, the angiosperm syringyl lignin DNA is fused to a constitutive promoter to form an expression cassette. The expression cassette is inserted into the gymnosperm genome to transform the gymnosperm genome. Cells containing the transformed genome are selected and used to produce a transformed gymnosperm plant containing syringyl lignin.

In accordance with the invention, the angiosperm gene sequences bi-OMT, 4CL, P450-1 and P-450-2 have been determined and isolated as associated with production of syringyl lignin in sweetgum and lignin promoter regions for the gymnosperm loblolly pine have been determined to be the 5' flanking regions for the 4CL1B, 4CL3B and PAL gymnosperm lignin genes. Expression cassettes containing sequences of selected genes from sweetgum have been inserted into loblolly pine embryogenic cells and presence of sweetgum genes associated with production of syringyl lignin has been confirmed in daughter cells of the resulting loblolly pine embryogenic cells.

The invention therefore enables production of gymnosperms such as loblolly pine containing genes which code for production of syringyl lignin, to thereby produce in such species syringyl lignin in the wood structure for enhanced pulpability.

BRIEF DESCRIPTION OF THE DRAWINGS

The above and other aspects of the invention will now be further described in the following detailed specification considered in conjunction with the following drawings in which:

FIGS. 2A-2E illustrate a bifunctional-O-methyl transferase (bi-OMT) gene sequence involved in the production of syringyl lignin in an angiosperm (SEQ ID 5 coding SEQ ID 6);

FIGS. 3A-3G illustrate a 4-coumarate CoA ligase (4CL) gene sequence involved in the production of syringyl lignin in an angiosperm (SEQ ID 7 coding SEQ ID 8);

FIG. 4 illustrates a ferulic acid-5-hydroxylase (P450-1) gene sequence involved in the production of syringyl lignin in an angiosperm (SEQ ID 1 coding SEQ ID 2);

FIG. 5 illustrates a ferulic acid-5-hydroxylase (P450-2) gene sequence involved in the production of syringyl lignin in an angiosperm (SEQ ID 3 coding SEQ ID 4);

FIG. 6 illustrates nucleotide sequences of the 5' flanking region of the loblolly pine 4CL3B gene showing the location of regulatory elements for lignin biosynthesis (SEQ ID NO: 10);

FIGS. 7A-7B illustrate nucleotide sequences of the 5' flanking region of the loblolly pine 4CL1B gene showing the location of regulatory elements for lignin biosynthesis (SEQ ID NO: 11);

FIGS. 8A-8B illustrate nucleotide sequences of the 5' flanking region of loblolly pine PAL gene showing the location of regulatory elements for lignin biosynthesis (SEQ ID 9);

FIG. 9 illustrates a PCR confirmation of the sweetgum P450-1 gene sequence in transgenic loblolly pine cells; and

DETAILED DESCRIPTION OF THE INVENTION

Figure 1:
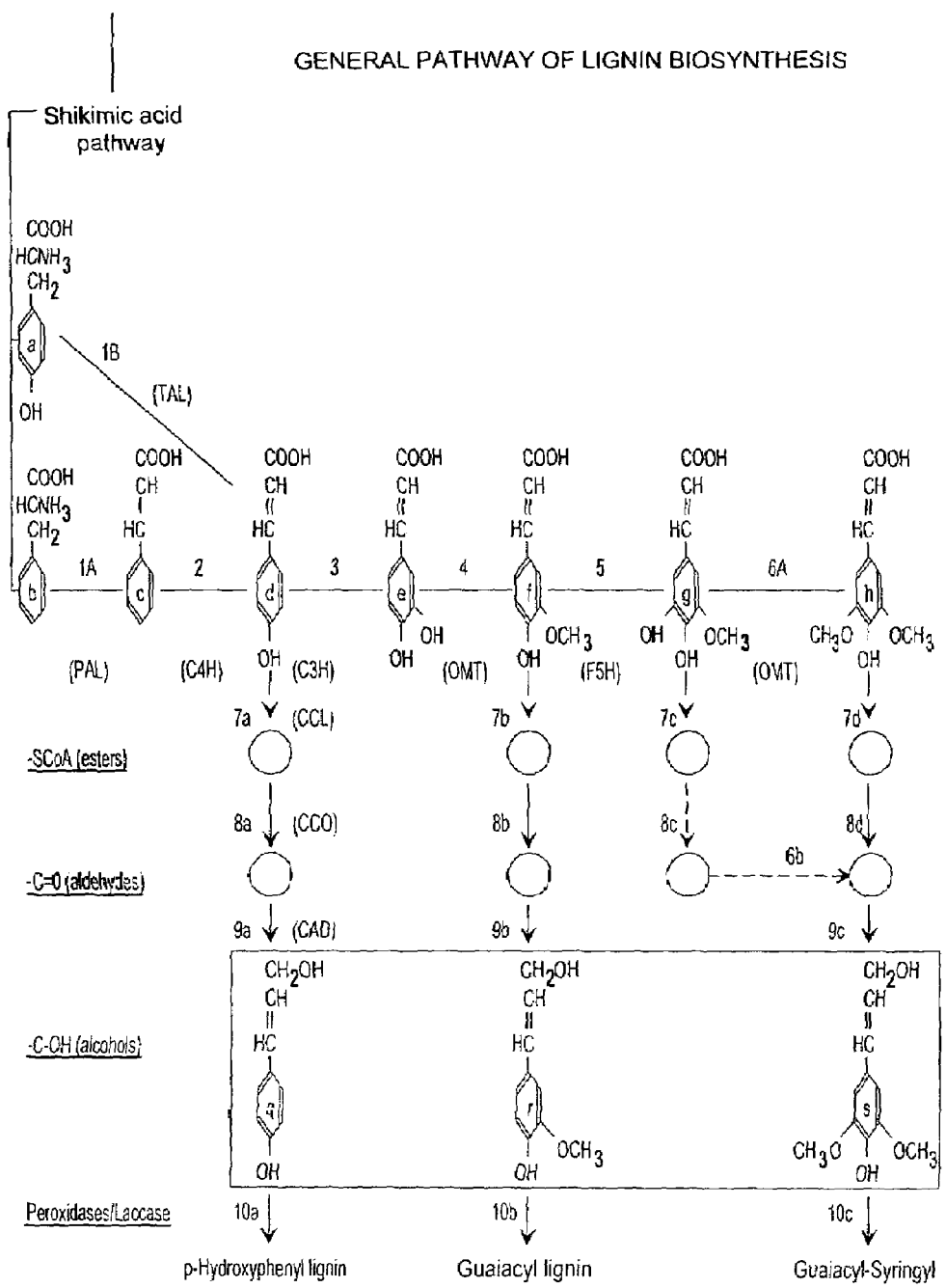
FIG. 1 illustrates a generalized pathway for lignin synthesis.

In accordance with the invention, a method is provided for modifying a gymnosperm genome, such as the genome of a loblolly pine, so that syringyl lignin will be produced in the resulting plant, thereby enabling cellulosic fibers of the same to be more easily separated from lignin in a pulping process. In general, this is accomplished by fusing one or more angiosperm DNA sequences (referred to at times herein as the "ASL DNA sequences") which are involved in production of syringyl lignin to a gymnosperm lignin promoter region (referred to at times herein as the "GL promoter region") specific to genes involved in gymnosperm lignin biosynthesis to form a gymnosperm syringyl lignin expression cassette (referred to at times herein as the "GSL expression cassette"). Alternatively, the one or more ASL DNA sequences are fused to one or more constitutive promoters to form a GSL expression cassette.

The GSL expression cassette preferably also includes selectable marker genes which enable transformed cells to be differentiated from untransformed cells. The GSL expression cassette containing selectable marker genes is inserted into the gymnosperm genome and transformed cells are identified and selected, from which whole gymnosperm plants may be produced which exhibit production of syringyl lignin.

To suppress production of less preferred forms of lignin in gymnosperms, such as guaiacyl lignin, genes from the gymnosperm associated with production of these less preferred forms of lignin are identified, isolated and the DNA sequence coding for anti-sense mRNA (referred to at times herein as the "GL anti-sense sequence") for these genes is produced. The DNA sequence coding for anti-sense mRNA is then incorporated into the gymnosperm genome, which when expressed bind to the less preferred guaiacyl gymnosperm lignin mRNA, inactivating it.

Further features of these and various other steps and procedures associated with practice of the invention will now be described in more detail beginning with identification and isolation of ASL DNA sequences of interest for use in inducing production of syringyl lignin in a gymnosperm.

I. DETERMINATION OF DNA SEQUENCE FOR GENES ASSOCIATED WITH PRODUCTION OF SYRINGYL LIGNIN

The general biosynthetic pathway for production of lignin has been postulated as shown in FIG. 1. From FIG. 1, it can be seen that the genes CCL, OMT and F5H (which is from the class of P450 genes) may play key roles in production of syringyl lignin in some plant species, but their specific contributions and mechanisms remain to be positively established. It is suspected that the CCL, OMT and F5H genes may have specific equivalents in a specific angiosperm, such as sweetgum. Accordingly, one aim of the present invention is to identify, sequence and clone specific genes of interest from an angiosperm such as sweetgum which are involved in production of syringyl lignin and to then introduce those genes into the genome of a gymnosperm, such as loblolly pine, to induce production of syringyl lignin.

Genes of interest may be identified in various ways, depending on how much information about the gene is already known. Genes believed to be associated with production of syringyl lignin have already been sequenced from a few angiosperm species, viz, CCL and OMT.

DNA sequences of the various CCL and OMT genes are compared to each other to determine if there are conserved regions. Once the conserved regions of the DNA sequences are identified, oligo-dT primers homologous to the conserved sequences are synthesized. Reverse transcription of the DNA-free total RNA which was purified from sweetgum xylem tissue, followed by double PCR using gene-specific primers, enables production of probes for the CCL and OMT genes.

A sweetgum cDNA library is constructed in a host, such as lambda ZAPII, available from Stratagene, of LaJolla, Calif., using poly(A)+ RNA isolated from sweetgum xylem, according to the methods described by Bugos et al. (1995 Biotechniques 19:734-737). The above mentioned probes are used to assay the sweetgum cDNA library to locate cDNA which codes for enzymes involved in production of syringyl lignin.

Once a syringyl lignin sequence is located, it is then cloned and sequenced according to known methods which are familiar to those of ordinary skill.

In accordance with the invention, two sweetgum syringyl lignin genes have been determined using the above-described technique. These genes have been designated 4CL and bi-OMT. The sequence obtained for the sweetgum syringyl lignin gene, designated bi-OMT, is illustrated in FIG. 2 (SEQ ID 5 and 6). The sequence obtained for the sweetgum syringyl lignin gene, designated 4CL, is illustrated in FIG. 3 (SEQ ID 7 and 8).

An alternative procedure was employed to identify the F5H equivalent genes in sweetgum. Because the DNA sequences for similar P450 genes from other plant species were known, probes for the P450 genes were designed based on the conserved regions found by comparing the known sequences for similar P450 genes. The known P450 sequences used for comparison include all plant P450 genes in the GenBank database. Primers were designed based on two highly conserved regions which are common to all known plant P450 genes. The primers were then used in a PCR reaction with the sweetgum cDNA library as a template. Once P450-like fragments were located, they were amplified using standard PCR techniques, cloned into a pBluescript vector available from Clonetech of Palo Alto, Calif. and transformed into a DH5.alpha. *E. coli* strain available from Gibco BRL of Gaithersburg, Md.

After *E. coli* colonies were tested in order to determine that they contained the P450-like DNA fragments, the fragments were sequenced. Several P450-like sequences were located in sweetgum using the above described technique. One P450-like sequence was sufficiently different from other known P450 sequences to indicate that it represented a new P450 gene family. This potentially new P450 cDNA fragment was used as a probe to screen a full length clone from the sweetgum xylem library. These putative hydroxylase P450clones were designated P450-1 and P450-2. The sequence obtained for P450-1 and P450-2 are illustrated in FIG. 4 (SEQ ID 1 and 2) and FIG. 5 (SEQ ID 3 and 4).

II. IDENTIFICATION OF GL GENE PROMOTER REGIONS

In order to locate gymnosperm lignin promoter regions, probes are developed to locate lignin genes. After the-gymnosperm lignin gene is located, the portion of DNA upstream from the gene is sequenced, preferably using the GenomeWalker Kit, available from Clonetech. The portion of DNA upstream from the lignin gene will generally contain the gymnosperm lignin promoter region.

Gymnosperm genes of interest include CCL-like genes and PAL-like genes, which are believed to be involved in the production of lignin in gymnosperms. Preferred probe sequences are developed based on previously sequenced genes, which are available from the gene bank. The preferred gene bank accession numbers for the CCL-like genes include U39404 and U39405. A preferred gene bank accession number for a PAL-like gene is U39792. Probes for such genes are constructed according to methods familiar to those of ordinary skill in the art. A genomic DNA library is constructed and DNA fragments which code for gymnosperm lignin genes are then identified using the above mentioned probes. A preferred DNA library is obtained from the gymnosperm, *Pinus taeda* (L.)[Loblolly Pine], and a preferred host of the genomic library is Lambda DashII, available from Stratagene of LaJolla, Calif.

Once the DNA fragments which code for the gymnosperm lignin genes are located, the genomic region upstream from the gymnosperm lignin gene (the 5' flanking region) was identified. This region contains the GL promoter. Three promoter regions were located from gymnosperm lignin biosynthesis genes. The first is the 5' flanking region of the loblolly pine 4CL3B gene, shown in FIG. 6 (SEQ ID NO: 10). The second is the 5' flanking region of the loblolly pine gene 4CL1B, shown in FIG. 7 FIGS. 7A-7B (SEQ ID NO: 11). The third is the 5' flanking region of the loblolly pine gene PAL, shown in FIG. 8 (SEQ ID NO: 9).

III. FUSING THE GL PROMOTER REGION TO THE ASL DNA SEQUENCE

The next step of the process is to fuse the GL promoter region to the ASL DNA sequence to make a GSL expression cassette for insertion into the genome of a gymnosperm. This may be accomplished by standard techniques. In a preferred method, the GL promoter region is first cloned into a suitable vector. Preferred vectors are pGEM7Z, available from Promega, Madison, Wis. and SK available from Stratagene, of LaJolla, Calif. After the promoter sequence is cloned into the vector, it is then released with suitable restriction enzymes. The ASL DNA sequence is released with the same restriction enzyme(s) and purified.

The GL promoter region sequence and the ASL DNA sequence are then ligated such as with T4 DNA ligase, available from Promega, to form the GSL expression cassette. Fusion of the GL and ASL DNA sequence is confirmed by restriction enzyme digestion and DNA sequencing. After confirmation of GL promoter-ASL DNA fusion, the GSL expression cassette is released from the original vector with suitable restriction enzymes and used in construction of vectors for plant transformation.

IV. FUSING THE ASL DNA SEQUENCE TO A CONSTITUTIVE PROMOTER REGION

In an alternative embodiment, a standard constitutive promoter may be fused with the ASL DNA sequence to make a GSL expression cassette. For example, a standard constitutive promoter may be fused with P450-1 to form an expression cassette for insertion of P450-1 sequences into a gymnosperm genome. In addition, a standard constitutive promoter may be fused with P450-2 to form an expression cassette for insertion of P450-2 into a gymnosperm genome. A constitutive promoter for use in the invention is the double 35S promoter, available from Clonetech.

In the preferred practice of the invention using constitutive promoters, a suitable vector such as pBI221, is digested XbaI and HindIII to release the 35S promoter. At the same time the vector pHygro, available from International Paper, was disgested by XbaI and HindIII to release the double 35S promoter. The double 35S promoter was ligated to the previously digested pBI221 vector to produce a new pBI221 with the double 35S promoter. This new pBI221 was digested with SacI and SmaI, to release the GUS fragment. The vector is next treated with T4 DNA polymerase to produce blunt ends and the vector is self-ligated. This vector is then further digested with BamHI and XbaI, available from Promega. After the pBI221 vector containing the constitutive promoter region has been prepared, lignin gene sequences are prepared for insertion into the pBI221 vector.

The coding regions of sweetgum P450-1 or P450-2 are amplified by PCR using primer with restriction sites incorporated in the 5' and 3' ends. In one example, an XbaI site was incorporated at the 5' end and a BamnHI site was incorporated at the 3' end of the sweetgum P450-1 or P450-2 genes. After PCR, the P450-1 and P450-2 genes were separately cloned into a TA vector available from Invitrogen. The TA vectors containing the P450-1 and P450-2 genes, respectively, were digested by XbaI and BamHI to release the P450-1 or P450-2 sequences.

The p35SS vector, described above, and the isolated sweetgum P450-1 or P450-2 fragments were then ligated to make GLS expression cassettes containing the constitutive promoter.

V. INSERTING THE EXPRESSION CASSETTE INTO THE GYMNOSPERM GENOME

There are a number of methods by which the GSL expression cassette may be inserted into a target gymnosperm cell. One method of inserting the expression cassette into the gymnosperm is by micro-projectile bombardment of gymnosperm cells. For example, embryogenic tissue cultures of loblolly pine may be initiated from immature zygotic embryos. Tissue is maintained in an undifferentiated state on semi-solid proliferation medium. For transformation, embryogenic tissue is s; suspended in liquid proliferation medium. Cells are then sieved through, a preferably 40 mesh screen, to separate small, densely cytoplasmic cells from large vacuolar cells.

After separation, a portion of the liquid cell suspension fraction is vacuum deposited onto filter paper and placed on semi-solid proliferation medium. The prepared gymnosperm target cells are then grown for several days on filter paper discs in a petri dish.

A 1:1 mixture of plasmid DNA containing the selectable marker expression cassette and plasmid DNA containing the P450-1 expression cassette may be precipitated with gold to form microprojectiles. The microprojectiles are rinsed in absolute ethanol and aliqots are dried onto a suitable macrocarrier such as the macrocarrier available from BioRad in Hercules, Calif.

Prior to bombardment, embryogenic tissue is preferably desiccated under a sterile laminar-flow hood. The desiccated tissue is transferred to semi-solid proliferation medium. The prepared microprojectiles are accelerated from the macrocarrier into the desiccated target cells using a suitable apparatus such as a BioRad PDS-1000/HE particle gun. In a preferred method, each plate is bombarded once, rotated 180 degrees, and bombarded a second time. Preferred bombardment parameters are 1350 psi rupture disc pressure, 6 mm distance from the rupture disc to macrocarrier (gap distance), 1 cm macrocarrier travel distance, and 10 cm distance from macrocarrier stopping screen to culture plate (microcarrier travel distance). Tissue is then transferred to semi-solid proliferation medium containing a selection agent, such as hygromycin B, for two days after bombardment.

Other methods of inserting the GSL expression cassette include use of silicon carbide whiskers, transformed protoplasts, *Agrobacterium* vectors and electroporation.

VI. IDENTIFYING TRANSFORMED CELLS

In general, insertion of the GSL expression cassette will typically be carried out in a mass of cells and it will be necessary to determine which cells harbor the recombinant DNA molecule containing the GSL expression cassette. Transformed cells are first identified by their ability to grow vigorously on a medium containing an antibiotic which is toxic to non-transformed cells. Preferred antibiotics are kanamycin and hygromycin B. Cells which grow vigorously on antibiotic containing medium are further tested for presence of either portions of the plasmid vector, the syringyl lignin genes in the GSL expression cassette; e.g. the angiosperm bi-OMT, 4CL, P450-1 or P450-2 gene, or by testing for presence of other fragments in the GSL expression cassette. Specific methods which can be used to test for presence of portions of the GSL expression cassette include Southern blotting with a labeled complementary probe or PCR amplification with specific complementary primers. In yet another approach, an expressed syringyl lignin enzyme can be detected by Western blotting with a specific antibody, or by assaying for a functional property such as the appearance of functional enzymatic activity.

VII. PRODUCTION OF A GYMNOSPERM PLANT FROM THE TRANSFORMED GYMNOSPERM CELL

Once transformed embryogenic cells of the gymnosperm have been identified, isolated and multiplied, they may be grown into plants. It is expected that all plants resulting from transformed cells will contain the GSL expression cassette in all their cells, and that wood in the secondary growth stage of the mature plant will be characterized by the presence of syringyl lignin.

Transgenic embryogenic cells are allowed to replicate and develop into a somatic embryo, which are then converted into a somatic seedling.

VIII. IDENTIFICATION, PRODUCTION AND INSERTION OF A GL mRNA ANTI-SENSE SEQUENCE

In addition to adding ASL DNA sequences, anti-sense sequences may be incorporated into a gymnosperm genome, via GSL expression cassettes, in order to suppress formation of the less preferred native gymnosperm lignin. To this end, the gymnosperm lignin gene is first located and sequenced in order to determine its nucleotide sequence. Methods for locating and sequencing amino acids which have been previously discussed may be employed. For example, if the gymnosperm lignin gene has already been purified, standard sequencing methods may be employed to determine the DNA nucleic acid sequence.

If the gymnosperm lignin gene has not been purified and functionally similar DNA or mRNA sequences from similar species are known, those sequences may be compared to identify highly conserved regions and this information used as a basis for the construction of a probe. A gymnosperm cDNA or genomic library can be probed with the above mentioned sequences to locate the gymnosperm lignin cDNA or genomic DNA. Once the gymnosperm lignin DNA is located, it may be sequenced using standard sequencing methods.

After the DNA sequence has been obtained for a gymnosperm lignin sequence, the complementary anti-sense strand is constructed and incorporated into an expression cassette. For example, the GL mRNA anti-sense sequence may be fused to a promoter region to form an expression cassette as described above. In a preferred method, the GL mRNA anti-sense sequence is incorporated into the previously discussed GSL expression cassette which is inserted into the gymnosperm genome as described above.

IX. INCLUSION OF CYTOCHROME P450 REDUCTASE (CPR) TO ENHANCE BIOSYNTHESIS OF SYRINGYL LIGNIN IN GYMNOSPERMS

In the absence of external cofactors such as NADPH (an electron donor in reductive biosyntheses), certain angiosperm lignin genes such as the P450 genes may remain inactive or not achieve full or desired activity after insertion into the genome of a gymnosperm. Inactivity or insufficient activity can be determined by testing the resulting plant which contains the P450 genes for the presence of syringyl lignin in secondary growth. It is known that cytochrome P450 reductase (CPR) may be involved in promoting certain reductive biochemical reactions, and may activate the desired expression of genes in many plants. Accordingly, if it is desired to enhance the expression of the angiosperm syringyl lignin genes in the gymnosperm, CPR may be inserted in the gymnosperm genome. In order to express CPR, the DNA sequence of the enzyme is ligated to a constitutive promoter or, for a specific species such as loblolly pine, xylem-specific lignin promoters such as PAL, 4CL1B or 4CL3B to form an expression cassette. The expression cassette may then be inserted into the gymnosperm genome by various methods as described above.

X. EXAMPLES

The following non-limiting examples illustrate further aspects of the invention. In these examples, the angiosperm is *Liquidambar styraciflua* (L.)[sweetgum] and the gymnosperm is *Pinus taeda* (L.)[loblolly pine]. The nomenclature for the genes referred to in the examples is as follows:

| Genes | Biochemical Name |
| --- | --- |
| 4CL (angiosperm) | 4-coumarate CoA ligase |
| bi-OMT (angiosperm) | bifunctional-O-methyl transferase |
| FA5H-1 (angiosperm) | ferulic acid-5-hydroxylase |
| FA5H-2 (angiosperm) | ferulic acid-5-hydroxylase |
| PAL (gymnosperm) | phenylalanine ammonia-lyase |
| 4CL1B (gymnosperm) | 4-coumarate CoA ligase |
| 4CL3B (gymnosperm) | 4-coumarate CoA ligase |

Example 1

Isolating and Sequencing bi-OMT and 4CL genes from an Angiosperm

A cDNA library for Sweetgum was constructed in Lambda ZAPII, available from Stratagene, of LaJolla, Calif., using poly(A)+RNA isolated from Sweetgum xylem tissue. Probes for bi-OMT and 4CL were obtained through reverse transcription of their mRNAs and followed by double PCR using gene-specific primers which were designed based on the OMT and CCL cDNA sequences obtained from similar genes cloned from other species.

Three primers were used for amplifying OMT fragments. One was an oligo-dT primer. One was a bi-OMT, (which was used to clone gene fragments through modified differential display technique, as described below in Example 2) and the other two were degenerate primers, which were based on the conserved sequences of all known OMTs. The two degenerate primers were derived based on the following amino acid sequences:

```
(primer #22)                          (SEQ ID 12)
5'-Gly Gly Met Ala Thr Tyr Cys Cys Ala Thr Thr Tyr
Ala Ala Cys Ala Ala Gly Gly Cys-3'
and (primer #23)                          (SEQ ID 13)
3'-Ala Ala Ala Gly Ala Gly Ala Gly Asn Ala Cys Asn
Asn Ala Asn Asn Ala Asn Gly Ala-5'.
```

A 900 bp PCR product was produced when oligo-dT primer and primer #22 were used a 550 bp fragment was produced when primer numbers 22 and 23 were used.

Three primers were used for amplifying CCL fragments. They were derived from the following amino acid sequences:

```
(primer R1S)                          (SEQ ID 14)
5'-Thr Thr Gly Gly Ala Thr Cys Cys Gly Gly Ile Ala
Cys Ile Ala Cys Ile Gly Gly Ile Tyr Thr Ile Cys
Cys Ile Ala Ala Arg Gly Gly-3'

(primer H1S)                          (SEQ ID 15)
5'-Thr Thr Gly Gly Ala Thr Cys Cys Gly Thr Ile Gly
Thr Ile Gly Cys Ile Cys Ala Arg Cys Ala Arg Gly
Thr Ile Gly Ala Tyr Gly Gly-3'
and (primer R2A)                          (SEQ ID 16)
3'-Cys Cys Ile Cys Thr Tyr Thr Ala Asp Ala Cys Arg
Thr Ala Asp Gly Cys Ile Cys Cys Ala Gly Cys Thr
Gly Thr Ala-5'
```

R1S and H1S were both sense primers. Primer R2A was an anti-sense primer. A 650 bp fragment was produced if R1S and R2A primers were used and a 550 bp fragment was produced when primers H1S and R2A were used. The sequence of these three primers were derived from conserved sequences for plant CCLs.

The reverse transcription-double PCR cloning technique used for these examples consisted of adding 10 μgf DNA-free total RNA in 25 μl DEPC-treated water to a microfuge tube. Next, the following solutions were added:
 a. 5× Reverse transcript buffer 8.0 μl,
 b. 0.1 M DTT 4.0 μl
 c. 10 mM dNTP 2.0 μl
 d. 100 μM oligo-dT primers 8.0 μl
 e. Rnasin 2.0 μl
 f. Superscript II 1.0 μl After mixing, the tube was incubated at a temperature of 42° C. for one (1) hour, followed by incubation at 70° C. for fifteen (15) minutes. Forty (40) μl of 1N NaOH was added and the tube was further incubated at 68° C. for twenty (20) minutes. After the incubation periods, 80 μl of 1N HCl was added to the reaction mixture. At the same time, 17 μl NaOAc, 5 μl glycogen and 768 μl of 100% ethanol were added and the reaction mixture was maintained at −80° C. for 15 minutes in order to precipitate the cDNA. The precipitated cDNA was centrifuged at high speed at 4° C. for 15 minutes. The resulting pellet was washed with 70% ethanol and then dried at room temperature, and then was dissolved in 20 μl of water.

The foregoing procedure produced purified cDNA which was used as a template to carry out first round PCR using primers #22 and oligo-dT for cloning OMT cDNA and primer R1S and R2A for cloning 4CL cDNA. For the first round PCR, a master mix of 50 μl for each reaction was prepared. Each 50 μl mixture contained:
 a. 10× buffer 5 μl
 b. 25 mM MgCl$_2$ 5 μl
 c. 100 μM sense primer 1 μl (primer #22 for OMT and primer R1S for CCL).

d. 1001 anti-sense primer 1 μl (oligo-dT primer for OMT and R2A for CCL).
e. 10 mM dNTP 1 μl
f. Taq. DNA polymerase 0.5 μl Of this master mix, 48 μl was added into a PCR tube containing 2 μl of cDNA for PCR. The tube was heated to 95° C. for 45 seconds, 52° C. for one minute and 72° C. for two minutes. This temperature cycle was repeated for 40 cycles and the mixture was then held at 72° C. for 10 minutes.

The cDNA fragments obtained from the first round of PCR were used as templates to perform the second round of PCR using primers 22 and 23 for cloning bi-OMT cDNA and primer H1S and R2A for cloning 4CL cDNA. The second round of PCR conditions were the same as the first round.

The desired cDNA fragment was then subcloned and sequenced. After the second round of PCR, the product with the predicted size was excised from the gel and ligated into a pUC19 vector, available from Clonetech, of Palo Alto, Calif., and then transformed into DH5.alpha., an *E. coli* strain, available from Gibco BRL, of Gaithersburg, Md. After the inserts had been checked for correct size, the colonies were isolated and plasmids were sequenced using a Sequenase kit available from USB, of Cleveland, Ohio. The sequences are shown in FIG. 2 (SEQ ID 5 and 6) and FIG. 3 (SEQ ID 7 and 8).

Example 2

Alternative Isolation Method of Angiosperm bi-OMT Gene

As previously mentioned, one bi-OMT clone was produced via modified differential display technique. This method is another type of reverse transcription-PCR, in which DNA-free total RNA was reverse transcribed using oligo-dT primers with a single base pair anchor to form cDNA. The oligo-dT primers used for reverse transcription of mRNA to synthesize cDNA were:

```
                                     (SEQ ID 17)
4 T11A: TTTTTTTTTTTTTA, (SEQ ID 18)
T11C: TTTTTTTTTTTTTC,
and (SEQ ID 19)
T11G: TTTTTTTTTTTTTG,
```

These cDNAs were then used as templates for radioactive PCR which was conducted in the presence of the same oligo-dT primers as listed above, a bi-OMT gene-specific primer and 35S-dATP. The OMT gene-specific primer was derived from the following amino acid sequence:

5'-Cys Cys Asn Gly Gly Asn Gly Gly Ser Ala Arg Gly Ala-3'. (SE ID 20)

The following PCR reaction solutions were combined in a microfuge tube:
a. H$_2$O 9.2 μl,
b. Taq Buffer 2.0 μl
c. dNTP (25 μM) 1.6 μl
d. Primers (5 μM) 2 μl, for each primer
e. $^{35}$S-dATP 1 μl
f. Taq. pol. 0.2 μl
g. cDNA 2.0 μl.

The tube was heated to a temperature of 94° C. and held for 45 seconds, then at 37° C. for 2 minutes and then 72° C. for 45 seconds for forty cycles, followed by a final reaction at 72° C. for 5 minutes.

The amplified products were fractionated on a denaturing polyacrylamide sequencing gel and autoradiography was used to identify and excise the fragments with a predicted size. The designed OMT gene-specific primer had a sequence conserved in a region toward the 3'-end of the OMT cDNA sequence. This primer, together with oligo-dT, was amplified into a OMT cDNA fragment of about 300 bp.

Three oligo-dTs with a single base pair of A, C or G, respectively, were used to pair with the OMT gene-specific primer. Eight potential OMT cDNA fragments with predicted sizes of about 300 bp were excised from the gels after several independent PCR rounds using different combinations of oligo-dT and OMT gene-specific oligo-nucleotides as primers.

The OMT cDNA fragments were then re-amplified. A Southern blot analysis was performed for the resulting cDNAs using a 360 base-pair, $^{32}$P radio-isotope labeled, aspen OMT cDNA 3'-end fragment as a probe to identify the cDNA fragments having a strong hybridization signal, under low stringency conditions. Eight fragments were identified. Out of these eight cDNA fragments, three were selected based on their high hybridization signal for sub-cloning and sequencing. One clone, LsOMT3'-1, (where the "Ls" prefix indicates that the clone was derived from the Liquidambar styraciflua (L.) genome) was confirmed to encode bi-OMT based on its high homology to other lignin-specific plant OMTs at both nucleotide and amino acid sequence levels.

A cDNA library was constructed in Lambda ZAP II, available from Stratagene, of LaJolla, Calif., using 5 mg poly(A)+ RNA isolated from sweetgum xylem tissue. The primary library consisting of approximately 0.7×10$^6$ independent recombinants was amplified and approximately 10$^5$ plaque-forming-units (pfu) were screened using a homologous 550 base-pair probe. The hybridized filter was washed at high stringency (0.25×SSC, 0.1% SDS, 65° C.) conditions. The colony containing the bi-OMT fragment identified by the probe was eluted and the bi-OMT fragment was produced. The sequence as illustrated in FIG. 2 (SEQ ID 5 and 6) was obtained.

Example 3

Isolating and Producing the DNA which Codes for the Angiosperm P450-1 Gene

In order to find putative P450 cDNA fragments as probes for cDNA library screening, a highly degenerated sense primer based on the amino acid sequence of 5'-Glu, Glu, Phe, Arg, Pro, Glu, Arg-3' was designed based on the conserved regions found in some plant P450 proteins. This conserved domain was located upstream of another highly conserved region in P450 proteins, which had an amino acid sequence of 5'-Phe Gly Xaa Gly Xaa Xaa Cys Xaa Gly-3' (SEQ ID 21). This primer was synthesized with the incorporation of an XboI restriction site to give a 26-base-pair oligomer with a nucleotide sequence of 5' ATG TGC AGT TTT TTT TTT TTT TIT TT-3' (SEQ ID 22).

This primer and the oligo-dT-XhoI primer were then used to perform PCR reactions with the sweetgum cDNA library as a template. The cDNA library was constructed in Lambda ZAPII, available from Stratagene, of LaJolla, Calif., using poly(a)+RNA isolated from Sweetgum xylem tissue. Amplified fragments of 300 to 600 bp were obtained. Because the designed primer was located upstream of the highly conserved P450 domain, this design distinguished whether the PCR products were P450 gene fragments depending on whether they contained the highly conserved amino acid domain.

All the fragments obtained from the PCR reaction were then cloned into a pUC19 vector, available from Stratagene, of LaJolla, Calif., and transformed into a DH5.alpha. $E.$ $coli$ strain, available from Gibco BRL, of Gaithersburg, Md.

Twenty-four positive colonies were obtained and sequenced. Sequence analysis indicated four groupings within the twenty-four colonies. One was C4H, one was an unknown P450 gene, and two did not belong to P450 genes. Homologies of P450 genes in different species are usually more than 80%. Because the homologies between the P450 gene families found here were around 40%, the sequence analysis indicated that a new P450 gene family was sequenced. Moreover, since this P450 cDNA was isolated from xylem tissue, it was highly probable that this P450 gene was P450-1.

The novel sweetgum P450 cDNA fragment was used as a probe to screen a full length cDNA encoding for P450-1. Once the P450-1 gene was located it was sequenced. The length of the P450-1 cDNA is 1707 bp and it contains 45 bp of 5' non-coding region and 135 bp of 3' non-coding region. The deduced amino acid sequence also indicates that this P450 cDNA has a hydrophobic core at the N-terminal, which could be regarded as a leader sequence for c-translational targeting to membranes during protein synthesis. At the C-terminal region, there is a heme binding domain that is characteristic of all P450 genes. The P450-1 sequence, as illustrated in FIG. 4 (SEQ ID 1 and 2), was produced, according to the above described methods.

Example 4

Isolating and Producing the DNA which Codes for the Angiosperm P450-2 Gene

By using similar strategy of synthesizing PCR primers from the published literature for hydroxylase genes in plants, another full length P450 cDNA has been isolated that shows significant similarity with a putitive F5H clone from $Arabidopsis$ (Meyers et al. 1996: PNAS 93, 6869-6874). This cloned cDNA, designated P450-2, contains 1883 bp and encodes an open reading frame of 511 amino acids. The amino acid similarity shared between $Arabidopsis$ FSH and the P450-2 sweetgum clone is about 75%.

To confirm the function of the P450-2 gene, it was expressed in $E.$ $coli$, strain, DH5 alpha, via pQE vector preparation, according to directions available with the kit. A CO—Fe2+binding assay was also performed to confirm the expression of P450-2 as a functional P450 gene. (Omura & Sato 1964, J. of Biochemistry 239: 2370-2378, Babriac et. al. 1991 Archives of Biochemistry and Biophysics 288:302-309). The CO—Fe2+ binding assay showed a peak at 450 nm which indicates that P450-2 has been overexpressed as a functional P450 gene.

The P450-2 protein was further purified for production of antibodies in rabbits, and antibodies have been successfully produced. In addition, Western blots show that this antibody is specific to the membrane fraction of sweetgum and aspen xylem extract. When the P450-2 antibody was added to a reaction mixture containing aspen xylem tissue, enzyme inhibition studies showed that the activity of P450 in aspen was reduced more than 60%, a further indication that P450-2 performs a p450 like function. Recombinant P450-2 protein co-expressed with $Arabidopsis$ CPR protein in a baculovirus expression system hydroxylated ferulic acid (specific activity: 7.3 pKat/mg protein), cinnaminic acid (specific activity: 25 pKat/mg protein, and p-coumeric acid (specific activity 3.8 pKat/ng protein). The P450-2 enzyme which may be referred to as C4C3F5-H appears to be a broad spectrum hydroxylase in the phenyproponoid pathway in plants FIG. 5 (SEQ ID 3 and 4) illustrates the P450-2 sequence.

Example 5

Identifying Gymnosperm Promoter Regions

In order to identify gymnosperm promoter regions, sequences from loblolly pine PAL and CL1B and 4CL3B lignin genes were used as primers to screen the loblolly pine genomic library, using the GenomeWalker Kit. The loblolly pine PAL primer sequence was obtained from the GenBank, reference number U39792. The loblolly pine 4CL1B primer sequences were also obtained from the gene bank, reference numbers U39404 and U39405.

The loblolly pine genomic library was constructed in Lambda DashII, available from Stratagene, of LaJolla, Calif. $3 \times 10^6$ phage plaques from the genomic library of loblolly pine were screened using both the above mentioned PAL cDNA and 4CL (PCR clone) fragments as probes. Five 4CL clones were obtained after screening. Lambda DNAs of two 4CL of the five 4CL clones obtained after screening were isolated and digested by EcoRV, Pstd, SalI and XbaI for Southern analysis. Southern analysis using 4CL fragments as probes indicated that both clones for the 4CL gene were identical. Results from further mapping showed that none of the original five 4CL clones contained promoter regions. When tested, the PAL clones obtained from the screening also did not contain promoter regions.

In a second attempt to clone the promoter regions associated with the PAL and 4CL a Universal GenomeWalker.™. kit, available from CLONETECH, was used. In the process, total DNA from loblolly pine was digested by several restriction enzymes and ligated into the adaptors (libraries) provided with the kit. Two gene-specific primers for each gene were designed (GSP1 and 2). After two rounds of PCR using these primers and adapter primers of the kit, several fragments were amplified from each library. A 1.6 kb fragment and a 0.6 kb fragment for PAL gene and a 2.3 kb fragment (4CL1B) and a 0.7 kb fragment (4CL3B) for the 4CL gene were cloned, sequenced and found to contain promoter regions for all three genes. See FIG. 6 (SEQ ID 10), 7 (SEQ ID 11) and 8 (SEQ ID 9).

Example 6

Fusing the ASL DNA Sequence to a Constitutive Promoter Region and Inserting the Expression Cassette Into a Gymnosperm Genome As a first step, a ASL DNA sequence, P450-1, was fused with a constitutive promoter region according to the methods described in the above Section IV to form an P450-1 expression cassette. A second ASL DNA sequence, P450-2, was then fused with a constitutive promoter in the same manner to form an P450-2 expression cassette. The P450-1 expression cassette was inserted into the gymnosperm genome by microprojectile bombardment. Embryogenic tissue cultures of loblolly pine were initiated from immature zygotic embryos. The tissue was maintained in an undifferentiated state on semi-solid proliferation medium, according to methods described by Newton et al. TAES Technical Publication "Somatic Embryogenesis in Slash Pine", 1995 and Keinonen-Mettala et al. 1996, Scand. J. For. Res. 11: 242-250.

After separation, 5 ml of the liquid cell suspension fraction which passes through the 40 mesh screen was vacuum deposited onto filter paper and placed on semi-solid proliferation medium. The prepared gymnosperm target cells were then grown for 2 days on filter paper discs placed on semi-solid proliferation medium in a petri dish. These target cell were then bombarded with plasmid DNA containing the P450-1 expression cassette and an expression cassette containing a selectable marker gene encoding the enzyme which confers resistance to the antibiotic hygromycin B. A 1:1 mixture of selectable marker expression cassette and plasmid DNA containing the P450-1 expression cassette is precipitated with gold (1.5-3.0 microns) as described by Sanford et al. (1992). The DNA-coated microprojectiles were rinsed in absolute ethanol and aliquots of 10 µl (5 µg DNA/3 mg gold) were dried onto a macrocarrier, such as those available from Bio-Rad (Hercules, Calif.).

Prior to bombardment, embryogenic tissue was desiccated under a sterile laminar-flow hood for 5 minutes. The desiccated tissue was transferred to semi-solid proliferation medium. The microprojectiles were accelerated into desiccated target cells using a BioRad PDS-1000/HE particle gun.

Each plate was bombarded once, rotated 180 degrees, and bombarded a second time. Preferred bombardment parameters were 1350 psi rupture disc pressure, 6 mm distance from the rupture disc to macrocarrier (gap distance), 1 cm macrocarrier travel distance, and 10 cm distance from macrocarrier stopping screen to culture plate (microcarrier travel distance). Tissue was then transferred to semi-solid proliferation medium containing hygromycin B for two days after bombardment.

The P450-2 expression cassette was inserted into the gymnosperm genome according to the same procedures.

Example 7

Selecting Transformed Target Cells

After insertion of the P450-1 expression cassette and the selectable marker expression cassette into the gymnosperm target cells as described in Example 6, transformed cells were selected by exposure to an antibiotic that causes mortality of any cells not containing the GSL expression cassette. Forty independent cell lines were established from cultures cobombarded with an expression cassette containing a hygromycin resistance gene construct and the P450-1 construct. These cell lines include lines Y2, Y17, Y7 and O4, as discussed in more detail below.

PCR techniques were then used to verify that the P450-1 gene had been successfully integrated into the genomes of the established cell lines by extracting genomic DNA using the Plant DNAeasy kit, available from Quaigen. 200 ng DNA from each cell line were used for each PCR reaction. Two P450-1 specific primers were designed to perform a PCR reaction with a 600 bp PCR product size. The primers were:

```
                                                (SEQ ID 23)
LsP450-im1-S primer: ATGGCTTTCCTTCTAATACCCATCTC,
and
                                                (SEQ ID 24)
LsP450-im1-A primer: GGGTGTAATGGACGAGCAAGGACTTG.
```

Each PCR reaction (100 µl) consisted of 75 µl H2O, 1 µl MgCl (25 mM), 10 µl PCR buffer 1 µl 10 mM dNTPs, and 10 µl DNA. 100 µl oil was layered on the top of each reaction mix. Hot start PCR was done as follows: PCR reaction was incubated at 95 degrees C. for 7 minutes and 1 µl each of both LsP450-im1-S and LsP450-im1-A primers (100 µM stock) and 1 µl of Taq polymerase were added through oil in each reaction. The PCR program used was 95 degrees C. for 1.5 minutes, 55 degrees C. for 45 sec and 72 degrees C. for 2 minutes, repeated for 40 cycles, followed by extension at 72 degrees C. for 10 minutes.

The above PCR products were employed to determine if gymnosperm cells contained the angiosperm lignin gene sequences. With reference to FIG. 9, PCR amplification was performed using template DNA from cells which grew vigorously on hygromycin B-containing medium. The PCR products were electrophoresed in an agarose gel containing 9 lanes. Lanes 14 contained PCR amplification of products of the Sweetgum P450-1 gene from a non-transformed control and transgenic loblolly pine cell lines. Lane 1 contained the non-transformed control PT52. Lane 2 contained transgenic line Y2. Lane 3 contained transgenic line Y17 and Lane 4 contained the plasmid which contains the expression cassette pSSLsP4501-im-s. Lanes 2 through 4 all contain an amplified fragment of about 600 bp, indicating that the P450-1 gene has been successfully inserted into transgenic cell lines Y2 and Y17.

Lane 5 contained a DNA size marker Phi 174/HaeII (BRL). The top four bands in this lane indicate molecular sizes of 1353, 1078, 872 and 603 bp.

Lanes 6-9 contained PCR amplification products of hygromycin B gene from non-transformed control and transgenic loblolly pine cell lines. Lane 6 contained the non-transformed control lane referenced to as PTS. Lane 7 contained transgenic line Y7. Lane 8 contained transgenic line O4. Lane 9 contained the plasmid which includes the expression cassette containing the gene encoding the enzyme which confers resistance tot he antibiotic hygromycin B. Lanes 7-9 all show an amplified fragment of about 1000 bp, indicating that the hygromycin gene has been successfully inserted into transgenic lines Y7 and O4.

These PCR results confirmed the presence of P450-1 and hygromycin resistance gene in transformed loblolly pine cell cultures. The results obtained from the PCR verification of 4 cell lines, and similar tests with the remaining 36 cell lines, confirm stable integration of the P450-1 gene and the hygromycin B gene in 25% of the 40 cell lines.

In addition, loblolly pine embryogenic cells which have been co-bombarded with the P450-2 and hygromycin B expression cassettes, are growing vigorously on hygromycin selection medium, indicating that the P450-2 expression cassette was successfully integrated into the gymnosperm genome.

Although various embodiments and features of the invention have been described in the foregoing detailed description, those of ordinary skill will recognize the invention is capable of numerous modifications, rearrangements and substitutions without departing from the scope of the invention as set forth in the appended claims. For example, in the case where the lignin DNA sequence is transcribed and translated to produce a functional syringyl lignin gene, those of ordinary skill will recognize that because of codon degeneracy a number of polynucleotide sequences will encode the same gene. These variants are intended to be covered by the DNA sequences disclosed and claimed herein. In addition, the sequences claimed herein include those sequences with encode a gene having substantial functional identity with those claimed. Thus, in the case of syringyl lignin genes, for example, the DNA sequences include variant polynucleotide sequences encoding polypeptides which have substantial identity with the amino acid sequence of syringyl lignin and which show syringyl lignin activity in gymnosperms.

What is claimed is:

1. An isolated promoter comprising SEQ ID NO: 10.

\* \* \* \* \*

SEQUENCE LISTING

```
<160> NUMBER OF SEQ ID NOS: 11

<210> SEQ ID NO 1
<211> LENGTH: 1708
<212> TYPE: DNA
<213> ORGANISM: Liquidambar styraciflua
<220> FEATURE:
<221> NAME/KEY: CDS
<222> LOCATION: (48)..(1571)

<400> SEQUENCE: 1
cggcacgagg aaaccctaaa actcacctct cttacccttt ctcttca atg gct ttc       56
                                                    Met Ala Phe
                                                      1 ctt cta ata ccc atc tca ata atc ttc atc gtc tta gct tac cag ctc      104
Leu Leu Ile Pro Ile Ser Ile Ile Phe Ile Val Leu Ala Tyr Gln Leu
      5                  10                  15 tat caa cgg ctc aga ttt aag ctc cca ccc ggc cca cgt cca tgg ccg      152
Tyr Gln Arg Leu Arg Phe Lys Leu Pro Pro Gly Pro Arg Pro Trp Pro
 20                  25                  30                  35 atc gtc gga aac ctt tac gac ata aaa ccg gtg agg ttc cgg tgt ttc      200
Ile Val Gly Asn Leu Tyr Asp Ile Lys Pro Val Arg Phe Arg Cys Phe
                 40                  45                  50 gcc gag tgg tca caa gcg tac ggt ccg atc ata tcg gtg tgg ttc ggt      248
Ala Glu Trp Ser Gln Ala Tyr Gly Pro Ile Ile Ser Val Trp Phe Gly
             55                  60                  65 tca acg ttg aat gtg atc gta tcg aat tcg gaa ttg gct aag gaa gtg      296
Ser Thr Leu Asn Val Ile Val Ser Asn Ser Glu Leu Ala Lys Glu Val
         70                  75                  80 ctc aag gaa aaa gat caa caa ttg gct gat agg cat agg agt aga tca      344
Leu Lys Glu Lys Asp Gln Gln Leu Ala Asp Arg His Arg Ser Arg Ser
     85                  90                  95 gct gcc aaa ttt agc agg gat ggg cag gac ctt ata tgg gct gat tat      392
Ala Ala Lys Phe Ser Arg Asp Gly Gln Asp Leu Ile Trp Ala Asp Tyr
100                 105                 110                 115 gga cct cac tat gtg aag gtt aca aag gtt tgt acc ctc gag ctt ttt      440
Gly Pro His Tyr Val Lys Val Thr Lys Val Cys Thr Leu Glu Leu Phe
                120                 125                 130 act cca aag cgg ctt gaa gct ctt aga ccc att aga gaa gat gaa gtt      488
Thr Pro Lys Arg Leu Glu Ala Leu Arg Pro Ile Arg Glu Asp Glu Val
            135                 140                 145 aca gcc atg gtt gag tcc att ttt aat gac act gcg aat cct gaa aat      536
Thr Ala Met Val Glu Ser Ile Phe Asn Asp Thr Ala Asn Pro Glu Asn
        150                 155                 160 tat ggg aag agt atg ctg gtg aag aag tat ttg gga gca gta gca ttc      584
Tyr Gly Lys Ser Met Leu Val Lys Lys Tyr Leu Gly Ala Val Ala Phe
    165                 170                 175 aac aac att aca aga ctc gca ttt gga aag cga ttc gtg aat tca gag      632
Asn Asn Ile Thr Arg Leu Ala Phe Gly Lys Arg Phe Val Asn Ser Glu
180                 185                 190                 195 ggt gta atg gac gag caa gga ctt gaa ttt aag gaa att gtg gcc aat      680
Gly Val Met Asp Glu Gln Gly Leu Glu Phe Lys Glu Ile Val Ala Asn
```

-continued

```
                      200                       205                        210
gga  ctc  aag  ctt  ggt  gcc  tca  ctt  gca  atg  gct  gag  cac  att  cct  tgg        728
Gly  Leu  Lys  Leu  Gly  Ala  Ser  Leu  Ala  Met  Ala  Glu  His  Ile  Pro  Trp
               215                      220                      225 ctc  cgt  tgg  atg  ttc  cca  ctt  gag  gaa  ggg  gcc  ttt  gcc  aag  cat  ggg        776
Leu  Arg  Trp  Met  Phe  Pro  Leu  Glu  Glu  Gly  Ala  Phe  Ala  Lys  His  Gly
               230                      235                      240 gca  cgt  agg  gac  cga  ctt  acc  aga  gct  atc  atg  gaa  gag  cac  aca  ata        824
Ala  Arg  Arg  Asp  Arg  Leu  Thr  Arg  Ala  Ile  Met  Glu  Glu  His  Thr  Ile
               245                      250                      255 gcc  cgt  aaa  aag  agt  ggt  gga  gcc  caa  caa  cat  ttc  gtg  gat  gca  ttg        872
Ala  Arg  Lys  Lys  Ser  Gly  Gly  Ala  Gln  Gln  His  Phe  Val  Asp  Ala  Leu
260                      265                      270                      275 ctc  acc  cta  caa  gag  aaa  tat  gac  ctt  agc  gag  gac  act  att  att  ggg        920
Leu  Thr  Leu  Gln  Glu  Lys  Tyr  Asp  Leu  Ser  Glu  Asp  Thr  Ile  Ile  Gly
               280                      285                      290 ctc  ctt  tgg  gat  atg  atc  act  gca  ggc  atg  gac  aca  acc  gca  atc  tct        968
Leu  Leu  Trp  Asp  Met  Ile  Thr  Ala  Gly  Met  Asp  Thr  Thr  Ala  Ile  Ser
               295                      300                      305 gtc  gaa  tgg  gcc  atg  gcc  gag  tta  att  aag  aac  cca  agg  gtg  caa  caa       1016
Val  Glu  Trp  Ala  Met  Ala  Glu  Leu  Ile  Lys  Asn  Pro  Arg  Val  Gln  Gln
               310                      315                      320 aaa  gct  caa  gag  gag  cta  gac  aat  gta  ctt  ggg  tcc  gaa  cgt  gtc  ctg       1064
Lys  Ala  Gln  Glu  Glu  Leu  Asp  Asn  Val  Leu  Gly  Ser  Glu  Arg  Val  Leu
325                      330                      335 acc  gaa  ttg  gac  ttc  tca  agc  ctc  cct  tat  cta  caa  tgt  gta  gcc  aag       1112
Thr  Glu  Leu  Asp  Phe  Ser  Ser  Leu  Pro  Tyr  Leu  Gln  Cys  Val  Ala  Lys
340                      345                      350                      355 gag  gca  cta  agg  ctg  cac  cct  cca  aca  cca  cta  atg  ctc  cct  cat  cgc       1160
Glu  Ala  Leu  Arg  Leu  His  Pro  Pro  Thr  Pro  Leu  Met  Leu  Pro  His  Arg
               360                      365                      370 gcc  aat  gcc  aac  gtc  aaa  att  ggt  ggc  tac  gac  atc  cct  aag  gga  tca       1208
Ala  Asn  Ala  Asn  Val  Lys  Ile  Gly  Gly  Tyr  Asp  Ile  Pro  Lys  Gly  Ser
               375                      380                      385 aat  gtt  cat  gta  aat  gtc  tgg  gcc  gtg  gct  cgt  gat  cca  gca  gtg  tgg       1256
Asn  Val  His  Val  Asn  Val  Trp  Ala  Val  Ala  Arg  Asp  Pro  Ala  Val  Trp
               390                      395                      400 cgt  gac  cca  cta  gag  ttt  cga  ccg  gaa  cgg  ttc  tct  gaa  gac  gat  gtc       1304
Arg  Asp  Pro  Leu  Glu  Phe  Arg  Pro  Glu  Arg  Phe  Ser  Glu  Asp  Asp  Val
405                      410                      415 gac  atg  aaa  ggt  cac  gat  tat  agg  cta  ctg  ccg  ttt  ggt  gca  ggg  agg       1352
Asp  Met  Lys  Gly  His  Asp  Tyr  Arg  Leu  Leu  Pro  Phe  Gly  Ala  Gly  Arg
420                      425                      430                      435 cgt  gtt  tgc  ccc  ggt  gca  caa  ctt  ggc  atc  aat  ttg  gtc  aca  tcc  atg       1400
Arg  Val  Cys  Pro  Gly  Ala  Gln  Leu  Gly  Ile  Asn  Leu  Val  Thr  Ser  Met
               440                      445                      450 atg  ggt  cac  cta  ttg  cac  cat  ttc  tat  tgg  agc  cct  cct  aaa  ggt  gta       1448
Met  Gly  His  Leu  Leu  His  His  Phe  Tyr  Trp  Ser  Pro  Pro  Lys  Gly  Val
               455                      460                      465 aaa  cca  gag  gag  att  gac  atg  tca  gag  aat  cca  gga  ttg  gtc  acc  tac       1496
Lys  Pro  Glu  Glu  Ile  Asp  Met  Ser  Glu  Asn  Pro  Gly  Leu  Val  Thr  Tyr
               470                      475                      480 atg  cga  acc  ccg  gtg  caa  gct  gtt  ccc  act  cca  agg  ctg  cct  gct  cac       1544
Met  Arg  Thr  Pro  Val  Gln  Ala  Val  Pro  Thr  Pro  Arg  Leu  Pro  Ala  His
485                      490                      495 ttg  tac  aaa  cgt  gta  gct  gtg  gat  atg  taattcttag tttgttatta                    1591
Leu  Tyr  Lys  Arg  Val  Ala  Val  Asp  Met
500                      505 ttcatgctct taaggttttg gactttgaac ttatgatgag atttgtaaaa ttccaagtga                    1651
```

-continued tcaaatgaag aaaagaccaa ataaaaaggc ttgacgattt aaaaaaaaaa aaaaaaa        1708

<210> SEQ ID NO 2
<211> LENGTH: 508
<212> TYPE: PRT
<213> ORGANISM: Liquidambar styraciflua

<400> SEQUENCE: 2

```
Met Ala Phe Leu Leu Ile Pro Ile Ser Ile Ile Phe Ile Val Leu Ala
 1               5                  10                  15

Tyr Gln Leu Tyr Gln Arg Leu Arg Phe Lys Leu Pro Pro Gly Pro Arg
                20                  25                  30

Pro Trp Pro Ile Val Gly Asn Leu Tyr Asp Ile Lys Pro Val Arg Phe
            35                  40                  45

Arg Cys Phe Ala Glu Trp Ser Gln Ala Tyr Gly Pro Ile Ile Ser Val
        50                  55                  60

Trp Phe Gly Ser Thr Leu Asn Val Ile Val Ser Asn Ser Glu Leu Ala
 65                  70                  75                  80

Lys Glu Val Leu Lys Glu Lys Asp Gln Gln Leu Ala Asp Arg His Arg
                85                  90                  95

Ser Arg Ser Ala Ala Lys Phe Ser Arg Asp Gly Gln Asp Leu Ile Trp
            100                 105                 110

Ala Asp Tyr Gly Pro His Tyr Val Lys Val Thr Lys Val Cys Thr Leu
        115                 120                 125

Glu Leu Phe Thr Pro Lys Arg Leu Glu Ala Leu Arg Pro Ile Arg Glu
    130                 135                 140

Asp Glu Val Thr Ala Met Val Glu Ser Ile Phe Asn Asp Thr Ala Asn
145                 150                 155                 160

Pro Glu Asn Tyr Gly Lys Ser Met Leu Val Lys Lys Tyr Leu Gly Ala
                165                 170                 175

Val Ala Phe Asn Asn Ile Thr Arg Leu Ala Phe Gly Lys Arg Phe Val
            180                 185                 190

Asn Ser Glu Gly Val Met Asp Glu Gln Gly Leu Glu Phe Lys Glu Ile
        195                 200                 205

Val Ala Asn Gly Leu Lys Leu Gly Ala Ser Leu Ala Met Ala Glu His
    210                 215                 220

Ile Pro Trp Leu Arg Trp Met Phe Pro Leu Glu Glu Gly Ala Phe Ala
225                 230                 235                 240

Lys His Gly Ala Arg Arg Asp Arg Leu Thr Arg Ala Ile Met Glu Glu
                245                 250                 255

His Thr Ile Ala Arg Lys Lys Ser Gly Gly Ala Gln Gln His Phe Val
            260                 265                 270

Asp Ala Leu Leu Thr Leu Gln Glu Lys Tyr Asp Leu Ser Glu Asp Thr
        275                 280                 285

Ile Ile Gly Leu Leu Trp Asp Met Ile Thr Ala Gly Met Asp Thr Thr
    290                 295                 300

Ala Ile Ser Val Glu Trp Ala Met Ala Glu Leu Ile Lys Asn Pro Arg
305                 310                 315                 320

Val Gln Gln Lys Ala Gln Glu Glu Leu Asp Asn Val Leu Gly Ser Glu
                325                 330                 335

Arg Val Leu Thr Glu Leu Asp Phe Ser Ser Leu Pro Tyr Leu Gln Cys
            340                 345                 350

Val Ala Lys Glu Ala Leu Arg Leu His Pro Pro Thr Pro Leu Met Leu
        355                 360                 365
```

```
Pro His Arg Ala Asn Ala Asn Val Lys Ile Gly Gly Tyr Asp Ile Pro
        370                 375                 380

Lys Gly Ser Asn Val His Val Asn Val Trp Ala Val Ala Arg Asp Pro
385                 390                 395                 400

Ala Val Trp Arg Asp Pro Leu Glu Phe Arg Pro Glu Arg Phe Ser Glu
                405                 410                 415

Asp Asp Val Asp Met Lys Gly His Asp Tyr Arg Leu Leu Pro Phe Gly
            420                 425                 430

Ala Gly Arg Arg Val Cys Pro Gly Ala Gln Leu Gly Ile Asn Leu Val
        435                 440                 445

Thr Ser Met Met Gly His Leu Leu His His Phe Tyr Trp Ser Pro Pro
    450                 455                 460

Lys Gly Val Lys Pro Glu Glu Ile Asp Met Ser Glu Asn Pro Gly Leu
465                 470                 475                 480

Val Thr Tyr Met Arg Thr Pro Val Gln Ala Val Pro Thr Pro Arg Leu
                485                 490                 495

Pro Ala His Leu Tyr Lys Arg Val Ala Val Asp Met
            500                 505

<210> SEQ ID NO 3
<211> LENGTH: 1883
<212> TYPE: DNA
<213> ORGANISM: Liquidambar styraciflua
<220> FEATURE:
<221> NAME/KEY: CDS
<222> LOCATION: (74)..(1606)

<400> SEQUENCE: 3
tgcaaacctg cacaaacaaa gagagagaag aagaaaaagg aagagaggag agagagagag      60
agagagagaa gcc atg gat tct tct ctt cat gaa gcc ttg caa cca cta       109
            Met Asp Ser Ser Leu His Glu Ala Leu Gln Pro Leu
              1               5                  10 ccc atg acg ctg ttc ttc att ata cct ttg cta ctc tta ttg ggc cta     157
Pro Met Thr Leu Phe Phe Ile Ile Pro Leu Leu Leu Leu Leu Gly Leu
        15                  20                  25 gta tct cgg ctt cgc cag aga cta cca tac cca cca ggc cca aaa ggc     205
Val Ser Arg Leu Arg Gln Arg Leu Pro Tyr Pro Pro Gly Pro Lys Gly
    30                  35                  40 tta ccg gtg atc gga aac atg ctc atg atg gat caa ctc act cac cga     253
Leu Pro Val Ile Gly Asn Met Leu Met Met Asp Gln Leu Thr His Arg
45                  50                  55                  60 gga ctc gcc aaa ctc gcc aaa caa tac ggc ggt cta ttc cac ctc aag     301
Gly Leu Ala Lys Leu Ala Lys Gln Tyr Gly Gly Leu Phe His Leu Lys
                65                  70                  75 atg gga ttc tta cac atg gtg gcc gtt tcc aca ccc gac atg gct cgc     349
Met Gly Phe Leu His Met Val Ala Val Ser Thr Pro Asp Met Ala Arg
        80                  85                  90 caa gtc ctt caa gtc caa gac aac atc ttc tcg aac cgg cca gcc acc     397
Gln Val Leu Gln Val Gln Asp Asn Ile Phe Ser Asn Arg Pro Ala Thr
    95                  100                 105 ata gcc atc agc tac ctc acc tat gac cga gcc gac atg gcc ttc gct     445
Ile Ala Ile Ser Tyr Leu Thr Tyr Asp Arg Ala Asp Met Ala Phe Ala
110                 115                 120 cac tac ggc ccg ttt tgg cgt cag atg cgt aaa ctc tgc gtc atg aaa     493
His Tyr Gly Pro Phe Trp Arg Gln Met Arg Lys Leu Cys Val Met Lys
125                 130                 135                 140 tta ttt agc cgg aaa cga gcc gag tcg tgg gag tcg gtc cga gac gag     541
Leu Phe Ser Arg Lys Arg Ala Glu Ser Trp Glu Ser Val Arg Asp Glu
```

-continued

```
                  145                 150                 155
gtc gac tcg gca gta cga gtg gtc gcg tcc aat att ggg tcg acg gtg         589
Val Asp Ser Ala Val Arg Val Val Ala Ser Asn Ile Gly Ser Thr Val
            160                 165                 170 aat atc ggc gag ctg gtt ttt gct ctg acg aag aat att act tac agg         637
Asn Ile Gly Glu Leu Val Phe Ala Leu Thr Lys Asn Ile Thr Tyr Arg
        175                 180                 185 gcg gct ttt ggg acg atc tcg cat gag gac cag gac gag ttc gtg gcc         685
Ala Ala Phe Gly Thr Ile Ser His Glu Asp Gln Asp Glu Phe Val Ala
    190                 195                 200 ata ctg caa gag ttt tcg cag ctg ttt ggt gct ttt aat ata gct gat         733
Ile Leu Gln Glu Phe Ser Gln Leu Phe Gly Ala Phe Asn Ile Ala Asp
205                 210                 215                 220 ttt atc cct tgg ctc aaa tgg gtt cct cag ggg att aac gtc agg ctc         781
Phe Ile Pro Trp Leu Lys Trp Val Pro Gln Gly Ile Asn Val Arg Leu
                225                 230                 235 aac aag gca cga ggg gcg ctt gat ggg ttt att gac aag atc atc gac         829
Asn Lys Ala Arg Gly Ala Leu Asp Gly Phe Ile Asp Lys Ile Ile Asp
            240                 245                 250 gat cat ata cag aag ggg agt aaa aac tcg gag gag gtt gat act gat         877
Asp His Ile Gln Lys Gly Ser Lys Asn Ser Glu Glu Val Asp Thr Asp
        255                 260                 265 atg gta gat gat tta ctt gct ttt tac ggt gag gaa gcc aaa gta agc         925
Met Val Asp Asp Leu Leu Ala Phe Tyr Gly Glu Glu Ala Lys Val Ser
    270                 275                 280 gaa tct gac gat ctt caa aat tcc atc aaa ctc acc aaa gac aac atc         973
Glu Ser Asp Asp Leu Gln Asn Ser Ile Lys Leu Thr Lys Asp Asn Ile
285                 290                 295                 300 aaa gct atc atg gac gta atg ttt gga ggg acc gaa acg gtg gcg tcc        1021
Lys Ala Ile Met Asp Val Met Phe Gly Gly Thr Glu Thr Val Ala Ser
                305                 310                 315 gcg att gaa tgg gcc atg acg gag ctg atg aaa agc cca gaa gat cta        1069
Ala Ile Glu Trp Ala Met Thr Glu Leu Met Lys Ser Pro Glu Asp Leu
            320                 325                 330 aag aag gtc caa caa gaa ctc gcc gtg gtg gtg ggt ctt gac cgg cga        1117
Lys Lys Val Gln Gln Glu Leu Ala Val Val Val Gly Leu Asp Arg Arg
        335                 340                 345 gtc gaa gag aaa gac ttc gag aag ctc acc tac ttg aaa tgc gta ctg        1165
Val Glu Glu Lys Asp Phe Glu Lys Leu Thr Tyr Leu Lys Cys Val Leu
    350                 355                 360 aag gaa gtc ctt cgc ctc cac cca ccc atc cca ctc ctc ctc cac gag        1213
Lys Glu Val Leu Arg Leu His Pro Pro Ile Pro Leu Leu Leu His Glu
365                 370                 375                 380 act gcc gag gac gcc gag gtc ggc ggc tac tac att ccg gcg aaa tcg        1261
Thr Ala Glu Asp Ala Glu Val Gly Gly Tyr Tyr Ile Pro Ala Lys Ser
                385                 390                 395 cgg gtg atg atc aac gcg tgc gcc atc ggc cgg gac aag aac tcg tgg        1309
Arg Val Met Ile Asn Ala Cys Ala Ile Gly Arg Asp Lys Asn Ser Trp
            400                 405                 410 gcc gac cca gat acg ttt agg ccc tcc agg ttt ctc aaa gac ggt gtg        1357
Ala Asp Pro Asp Thr Phe Arg Pro Ser Arg Phe Leu Lys Asp Gly Val
        415                 420                 425 ccc gat ttc aaa ggg aac aac ttc gag ttc atc cca ttc ggg tca ggt        1405
Pro Asp Phe Lys Gly Asn Asn Phe Glu Phe Ile Pro Phe Gly Ser Gly
    430                 435                 440 cgt cgg tct tgc ccc ggt atg caa ctc gga ctc tac gcg cta gag acg        1453
Arg Arg Ser Cys Pro Gly Met Gln Leu Gly Leu Tyr Ala Leu Glu Thr
445                 450                 455                 460 act gtg gct cac ctc ctt cac tgt ttc acg tgg gag ttg ccg gac ggg        1501
```

```
                Thr Val Ala His Leu Leu His Cys Phe Thr Trp Glu Leu Pro Asp Gly
                            465                 470                 475 atg aaa ccg agt gaa ctc gag atg aat gat gtg ttt gga ctc acc gcg      1549
                Met Lys Pro Ser Glu Leu Glu Met Asn Asp Val Phe Gly Leu Thr Ala
                            480                 485                 490 cca aga gcg att cga ctc acc gcc gtg ccg agt cca cgc ctt ctc tgt      1597
                Pro Arg Ala Ile Arg Leu Thr Ala Val Pro Ser Pro Arg Leu Leu Cys
                        495                 500                 505 cct ctc tat tgatcgaatg attggggag ctttgtggag ggcttttat                1646
                Pro Leu Tyr
                        510 ggagactcta tatatagatg ggaagtgaaa caacgacagg tgaatgcttg gattttggt      1706 atatattggg gagggagggg aaaaaaaaaa taatgaaagg aagaaaaga gagaatttga      1766 atttctcttc ctctgtggat aaaagcctcg tttttaattg tttttatgtg gagatatttg      1826 tgtttgttta ttttatctc tttttttgca ataacactca aaataaaaa aaaaaaa         1883

<210> SEQ ID NO 4
                <211> LENGTH: 511
                <212> TYPE: PRT
                <213> ORGANISM: Liquidambar styraciflua

<400> SEQUENCE: 4

Met Asp Ser Ser Leu His Glu Ala Leu Gln Pro Leu Pro Met Thr Leu
                 1               5                   10                  15

Phe Phe Ile Ile Pro Leu Leu Leu Leu Gly Leu Val Ser Arg Leu
                            20                  25                  30

Arg Gln Arg Leu Pro Tyr Pro Pro Gly Pro Lys Gly Leu Pro Val Ile
                        35                  40                  45

Gly Asn Met Leu Met Met Asp Gln Leu Thr His Arg Gly Leu Ala Lys
                    50                  55                  60

Leu Ala Lys Gln Tyr Gly Gly Leu Phe His Leu Lys Met Gly Phe Leu
                 65                 70                  75                  80

His Met Val Ala Val Ser Thr Pro Asp Met Ala Arg Gln Val Leu Gln
                                85                  90                  95

Val Gln Asp Asn Ile Phe Ser Asn Arg Pro Ala Thr Ile Ala Ile Ser
                            100                 105                 110

Tyr Leu Thr Tyr Asp Arg Ala Asp Met Ala Phe Ala His Tyr Gly Pro
                        115                 120                 125

Phe Trp Arg Gln Met Arg Lys Leu Cys Val Met Lys Leu Phe Ser Arg
                    130                 135                 140

Lys Arg Ala Glu Ser Trp Glu Ser Val Arg Asp Glu Val Asp Ser Ala
                145                 150                 155                 160

Val Arg Val Val Ala Ser Asn Ile Gly Ser Thr Val Asn Ile Gly Glu
                                165                 170                 175

Leu Val Phe Ala Leu Thr Lys Asn Ile Thr Tyr Arg Ala Ala Phe Gly
                            180                 185                 190

Thr Ile Ser His Glu Asp Gln Asp Glu Phe Val Ala Ile Leu Gln Glu
                        195                 200                 205

Phe Ser Gln Leu Phe Gly Ala Phe Asn Ile Ala Asp Phe Ile Pro Trp
                    210                 215                 220

Leu Lys Trp Val Pro Gln Gly Ile Asn Val Arg Leu Asn Lys Ala Arg
                225                 230                 235                 240

Gly Ala Leu Asp Gly Phe Ile Asp Lys Ile Ile Asp Asp His Ile Gln
                                245                 250                 255
```

-continued

```
Lys Gly Ser Lys Asn Ser Glu Glu Val Asp Thr Asp Met Val Asp Asp
            260                 265                 270

Leu Leu Ala Phe Tyr Gly Glu Ala Lys Val Ser Glu Ser Asp Asp
        275                 280                 285

Leu Gln Asn Ser Ile Lys Leu Thr Lys Asp Asn Ile Lys Ala Ile Met
        290                 295                 300

Asp Val Met Phe Gly Gly Thr Glu Thr Val Ala Ser Ala Ile Glu Trp
305                 310                 315                 320

Ala Met Thr Glu Leu Met Lys Ser Pro Glu Asp Leu Lys Lys Val Gln
                325                 330                 335

Gln Glu Leu Ala Val Val Gly Leu Asp Arg Arg Val Glu Lys
            340                 345                 350

Asp Phe Glu Lys Leu Thr Tyr Leu Lys Cys Val Leu Lys Glu Val Leu
            355                 360                 365

Arg Leu His Pro Pro Ile Pro Leu Leu Leu His Glu Thr Ala Glu Asp
        370                 375                 380

Ala Glu Val Gly Gly Tyr Tyr Ile Pro Ala Lys Ser Arg Val Met Ile
385                 390                 395                 400

Asn Ala Cys Ala Ile Gly Arg Asp Lys Asn Ser Trp Ala Asp Pro Asp
                405                 410                 415

Thr Phe Arg Pro Ser Arg Phe Leu Lys Asp Gly Val Pro Asp Phe Lys
            420                 425                 430

Gly Asn Asn Phe Glu Phe Ile Pro Phe Gly Ser Gly Arg Arg Ser Cys
        435                 440                 445

Pro Gly Met Gln Leu Gly Leu Tyr Ala Leu Glu Thr Thr Val Ala His
    450                 455                 460

Leu Leu His Cys Phe Thr Trp Glu Leu Pro Asp Gly Met Lys Pro Ser
465                 470                 475                 480

Glu Leu Glu Met Asn Asp Val Phe Gly Leu Thr Ala Pro Arg Ala Ile
                485                 490                 495

Arg Leu Thr Ala Val Pro Ser Pro Arg Leu Leu Cys Pro Leu Tyr
            500                 505                 510
```

<210> SEQ ID NO 5
<211> LENGTH: 1380
<212> TYPE: DNA
<213> ORGANISM: Liquidambar styraciflua
<220> FEATURE:
<221> NAME/KEY: CDS
<222> LOCATION: (67)..(1170)

<400> SEQUENCE: 5

```
cggcacgagc cctacctcct ttcttggaaa aatttcccca ttcgatcaca atccgggcct    60 caaaaa atg gga tca aca agc gaa acg aag atg agc ccg agt gaa gca   108
       Met Gly Ser Thr Ser Glu Thr Lys Met Ser Pro Ser Glu Ala
         1               5                  10 gca gca gca gaa gaa gaa gca ttc gta ttc gct atg caa tta acc agt   156
Ala Ala Ala Glu Glu Glu Ala Phe Val Phe Ala Met Gln Leu Thr Ser
 15                  20                  25                  30 gct tca gtt ctt ccc atg gtc cta aaa tca gcc ata gag ctc gac gtc   204
Ala Ser Val Leu Pro Met Val Leu Lys Ser Ala Ile Glu Leu Asp Val
                 35                  40                  45 tta gaa atc atg gct aaa gct ggt cca ggt gcg cac ata tcc aca tct   252
Leu Glu Ile Met Ala Lys Ala Gly Pro Gly Ala His Ile Ser Thr Ser
             50                  55                  60 gac ata gcc tct aag ctg ccc aca aag aat cca gat gca gcc gtc atg   300
Asp Ile Ala Ser Lys Leu Pro Thr Lys Asn Pro Asp Ala Ala Val Met
         65                  70                  75
```

```
                65                    70                    75
ctt gac cgt atg ctc cgc ctc ttg gct agc tac tct gtt cta acg tgc         348
Leu Asp Arg Met Leu Arg Leu Leu Ala Ser Tyr Ser Val Leu Thr Cys
         80                    85                    90 tct ctc cgc acc ctc cct gac ggc aag atc gag agg ctt tac ggc ctt         396
Ser Leu Arg Thr Leu Pro Asp Gly Lys Ile Glu Arg Leu Tyr Gly Leu
 95                   100                   105                   110 gca ccc gtt tgt aaa ttc ttg acc aga aac gat gat gga gtc tcc ata         444
Ala Pro Val Cys Lys Phe Leu Thr Arg Asn Asp Asp Gly Val Ser Ile
                     115                   120                   125 gcc gct ctg tct ctc atg aat caa gac aag gtc ctc atg gag agc tgg         492
Ala Ala Leu Ser Leu Met Asn Gln Asp Lys Val Leu Met Glu Ser Trp
                130                   135                   140 tac cac ttg acc gag gca gtt ctt gaa ggt gga att cca ttt aac aag         540
Tyr His Leu Thr Glu Ala Val Leu Glu Gly Gly Ile Pro Phe Asn Lys
            145                   150                   155 gcc tat gga atg aca gca ttt gag tac cat ggc acc gat ccc aga ttc         588
Ala Tyr Gly Met Thr Ala Phe Glu Tyr His Gly Thr Asp Pro Arg Phe
        160                   165                   170 aac aca gtt ttc aac aat gga atg tcc aat cat tcg acc att acc atg         636
Asn Thr Val Phe Asn Asn Gly Met Ser Asn His Ser Thr Ile Thr Met
175                   180                   185                   190 aag aaa atc ctt gag act tac aaa ggg ttc gag gga ctt gga tct gtg         684
Lys Lys Ile Leu Glu Thr Tyr Lys Gly Phe Glu Gly Leu Gly Ser Val
                 195                   200                   205 gtt gat gtt ggt ggt ggc act ggt gcc cac ctt aac atg att atc gct         732
Val Asp Val Gly Gly Gly Thr Gly Ala His Leu Asn Met Ile Ile Ala
            210                   215                   220 aaa tac ccc atg atc aag ggc att aac ttc gac ttg cct cat gtt att         780
Lys Tyr Pro Met Ile Lys Gly Ile Asn Phe Asp Leu Pro His Val Ile
        225                   230                   235 gag gag gct ccc tcc tat cct ggt gtg gag cat gtt ggt gga gat atg         828
Glu Glu Ala Pro Ser Tyr Pro Gly Val Glu His Val Gly Gly Asp Met
    240                   245                   250 ttt gtt agt gtt cca aaa gga gat gcc att ttc atg aag tgg ata tgt         876
Phe Val Ser Val Pro Lys Gly Asp Ala Ile Phe Met Lys Trp Ile Cys
255                   260                   265                   270 cat gat tgg agc gat gaa cac tgc ttg aag ttt ttg aag aaa tgt tat         924
His Asp Trp Ser Asp Glu His Cys Leu Lys Phe Leu Lys Lys Cys Tyr
                275                   280                   285 gaa gca ctt cca acc aat ggg aag gtg atc ctt gct gaa tgc atc ctc         972
Glu Ala Leu Pro Thr Asn Gly Lys Val Ile Leu Ala Glu Cys Ile Leu
            290                   295                   300 ccc gtg gcg cca gac gca agc ctc ccc act aag gca gtg gtc cat att        1020
Pro Val Ala Pro Asp Ala Ser Leu Pro Thr Lys Ala Val Val His Ile
        305                   310                   315 gat gtc atc atg ttg gct cat aac cca ggt ggg aaa gag aga act gag        1068
Asp Val Ile Met Leu Ala His Asn Pro Gly Gly Lys Glu Arg Thr Glu
    320                   325                   330 aag gag ttt gag gcc ttg gcc aag ggg gct gga ttt gaa ggt ttc cga        1116
Lys Glu Phe Glu Ala Leu Ala Lys Gly Ala Gly Phe Glu Gly Phe Arg
335                   340                   345                   350 gta gta gcc tcg tgc gct tac aat aca tgg atc atc gaa ttt ttg aag        1164
Val Val Ala Ser Cys Ala Tyr Asn Thr Trp Ile Ile Glu Phe Leu Lys
                355                   360                   365 aag att tgagtcctta ctcggctttg agtacataat accaactcct tttggttttc        1220
Lys Ile gagattgtga ttgtgattgt gattgtctct ctttcgcagt tggccttatg atataatgta     1280
```

```
tcgttaactc gatcacagaa gtgcaaaaga cagtgaatgt acactgcttt ataaaataaa    1340
aattttaaga ttttgattca tgtaaaaaaa aaaaaaaaaa                          1380
```

<210> SEQ ID NO 6
<211> LENGTH: 368
<212> TYPE: PRT
<213> ORGANISM: Liquidambar styraciflua

<400> SEQUENCE: 6

```
Met Gly Ser Thr Ser Glu Thr Lys Met Ser Pro Ser Glu Ala Ala Ala
 1               5                  10                  15

Ala Glu Glu Glu Ala Phe Val Phe Ala Met Gln Leu Thr Ser Ala Ser
             20                  25                  30

Val Leu Pro Met Val Leu Lys Ser Ala Ile Glu Leu Asp Val Leu Glu
         35                  40                  45

Ile Met Ala Lys Ala Gly Pro Gly Ala His Ile Ser Thr Ser Asp Ile
     50                  55                  60

Ala Ser Lys Leu Pro Thr Lys Asn Pro Asp Ala Ala Val Met Leu Asp
 65                  70                  75                  80

Arg Met Leu Arg Leu Leu Ala Ser Tyr Ser Val Leu Thr Cys Ser Leu
                 85                  90                  95

Arg Thr Leu Pro Asp Gly Lys Ile Glu Arg Leu Tyr Gly Leu Ala Pro
            100                 105                 110

Val Cys Lys Phe Leu Thr Arg Asn Asp Asp Gly Val Ser Ile Ala Ala
        115                 120                 125

Leu Ser Leu Met Asn Gln Asp Lys Val Leu Met Glu Ser Trp Tyr His
130                 135                 140

Leu Thr Glu Ala Val Leu Glu Gly Gly Ile Pro Phe Asn Lys Ala Tyr
145                 150                 155                 160

Gly Met Thr Ala Phe Glu Tyr His Gly Thr Asp Pro Arg Phe Asn Thr
                165                 170                 175

Val Phe Asn Asn Gly Met Ser Asn His Ser Thr Ile Thr Met Lys Lys
            180                 185                 190

Ile Leu Glu Thr Tyr Lys Gly Phe Glu Gly Leu Gly Ser Val Val Asp
        195                 200                 205

Val Gly Gly Gly Thr Gly Ala His Leu Asn Met Ile Ile Ala Lys Tyr
    210                 215                 220

Pro Met Ile Lys Gly Ile Asn Phe Asp Leu Pro His Val Ile Glu Glu
225                 230                 235                 240

Ala Pro Ser Tyr Pro Gly Val Glu His Val Gly Gly Asp Met Phe Val
                245                 250                 255

Ser Val Pro Lys Gly Asp Ala Ile Phe Met Lys Trp Ile Cys His Asp
            260                 265                 270

Trp Ser Asp Glu His Cys Leu Lys Phe Leu Lys Cys Tyr Glu Ala
        275                 280                 285

Leu Pro Thr Asn Gly Lys Val Ile Leu Ala Glu Cys Ile Leu Pro Val
    290                 295                 300

Ala Pro Asp Ala Ser Leu Pro Thr Lys Ala Val Val His Ile Asp Val
305                 310                 315                 320

Ile Met Leu Ala His Asn Pro Gly Gly Lys Glu Arg Thr Glu Lys Glu
                325                 330                 335

Phe Glu Ala Leu Ala Lys Gly Ala Gly Phe Glu Gly Phe Arg Val Val
            340                 345                 350

Ala Ser Cys Ala Tyr Asn Thr Trp Ile Ile Glu Phe Leu Lys Lys Ile
```

-continued

```
           355              360              365

<210> SEQ ID NO 7
<211> LENGTH: 2025
<212> TYPE: DNA
<213> ORGANISM: Liquidambar styraciflua
<220> FEATURE:
<221> NAME/KEY: CDS
<222> LOCATION: (60)..(1679)

<400> SEQUENCE: 7
cggcacgagc tcattttcca cttctggttt gatctctgca attcttccat cagtccta      59 atg gag acc caa aca aaa caa gaa gaa atc ata tat cgg tcg aaa ctc     107
Met Glu Thr Gln Thr Lys Gln Glu Glu Ile Ile Tyr Arg Ser Lys Leu
 1               5                  10                  15 ccc gat atc tac atc ccc aaa cac ctc cct tta cat tcg tat tgt ttc     155
Pro Asp Ile Tyr Ile Pro Lys His Leu Pro Leu His Ser Tyr Cys Phe
                20                  25                  30 gag aac atc tca cag ttc ggc tcc cgc ccc tgt ctg atc aat ggc gca     203
Glu Asn Ile Ser Gln Phe Gly Ser Arg Pro Cys Leu Ile Asn Gly Ala
            35                  40                  45 acg ggc aag tat tac aca tat gct gag gtt gag ctc att gcg cgc aag     251
Thr Gly Lys Tyr Tyr Thr Tyr Ala Glu Val Glu Leu Ile Ala Arg Lys
        50                  55                  60 gtc gca tcc ggc ctc aac aaa ctc ggc gtt cga caa ggt gac atc atc     299
Val Ala Ser Gly Leu Asn Lys Leu Gly Val Arg Gln Gly Asp Ile Ile
 65                  70                  75                  80 atg ctt ttg cta ccc aac tcg ccg gag ttc gtg ttt tca att ctc ggc     347
Met Leu Leu Leu Pro Asn Ser Pro Glu Phe Val Phe Ser Ile Leu Gly
                85                  90                  95 gca tcc tac cgc ggg gct gcc gcc acc gcc gca aac ccg ttt tat acc     395
Ala Ser Tyr Arg Gly Ala Ala Ala Thr Ala Ala Asn Pro Phe Tyr Thr
                100                 105                 110 cct gcc gag atc agg aag caa gcc aaa acc tcc aac gcc agg ctt att     443
Pro Ala Glu Ile Arg Lys Gln Ala Lys Thr Ser Asn Ala Arg Leu Ile
            115                 120                 125 atc aca cat gcc tgt tac tat gag aaa gtg aag gac ttg gtg gaa gag     491
Ile Thr His Ala Cys Tyr Tyr Glu Lys Val Lys Asp Leu Val Glu Glu
        130                 135                 140 aac gtt gcc aag atc ata tgt ata gac tca ccc ccg gac ggt tgt ttg     539
Asn Val Ala Lys Ile Ile Cys Ile Asp Ser Pro Pro Asp Gly Cys Leu
145                 150                 155                 160 cac ttc tcg gag ctg agt gag gcg gac gag aac gac atg ccc aat gta     587
His Phe Ser Glu Leu Ser Glu Ala Asp Glu Asn Asp Met Pro Asn Val
                165                 170                 175 gag att gac ccc gat gat gtg gtg gcg ctg ccg tac tcg tca ggg acg     635
Glu Ile Asp Pro Asp Asp Val Val Ala Leu Pro Tyr Ser Ser Gly Thr
            180                 185                 190 acg ggt tta cca aag ggg gtg atg cta aca cac aag gga caa gtg acg     683
Thr Gly Leu Pro Lys Gly Val Met Leu Thr His Lys Gly Gln Val Thr
        195                 200                 205 agt gtg gcg caa cag gtg gac gga gag aat ccg aac ctg tat ata cat     731
Ser Val Ala Gln Gln Val Asp Gly Glu Asn Pro Asn Leu Tyr Ile His
    210                 215                 220 agc gag gac gtg gtt ctg tgc gtg ttg cct ctg ttt cac atc tac tcg     779
Ser Glu Asp Val Val Leu Cys Val Leu Pro Leu Phe His Ile Tyr Ser
225                 230                 235                 240 atg aac gtc atg ttt tgc ggg tta cga gtt ggt gcg gcg att ctg att     827
Met Asn Val Met Phe Cys Gly Leu Arg Val Gly Ala Ala Ile Leu Ile
                245                 250                 255
```

```
atg cag aaa ttt gaa ata tat ggg ttg tta gag ctg gtc aga agt aca      875
Met Gln Lys Phe Glu Ile Tyr Gly Leu Leu Glu Leu Val Arg Ser Thr
        260                 265                 270 ggt gac cat cat gcc tat cgt aca ccc atc gta ttg gca atc tcc aag      923
Gly Asp His His Ala Tyr Arg Thr Pro Ile Val Leu Ala Ile Ser Lys
                275                 280                 285 act ccg gat ctt cac aac tat gat gtg tcc tcc att cgg act gtc atg      971
Thr Pro Asp Leu His Asn Tyr Asp Val Ser Ser Ile Arg Thr Val Met
        290                 295                 300 tca ggt gcg gct cct ctg ggc aag gaa ctt gaa gat tct gtc aga gct     1019
Ser Gly Ala Ala Pro Leu Gly Lys Glu Leu Glu Asp Ser Val Arg Ala
305                 310                 315                 320 aag ttt ccc acc gcc aaa ctt ggt cag gga tat gga atg acg gag gca     1067
Lys Phe Pro Thr Ala Lys Leu Gly Gln Gly Tyr Gly Met Thr Glu Ala
                325                 330                 335 ggg ccc gtg cta gcg atg tgt ttg gca ttt gcc aag gaa ggg ttt gaa     1115
Gly Pro Val Leu Ala Met Cys Leu Ala Phe Ala Lys Glu Gly Phe Glu
            340                 345                 350 ata aaa tcg ggg gca tct gga act gtt tta agg aac gca cag atg aag     1163
Ile Lys Ser Gly Ala Ser Gly Thr Val Leu Arg Asn Ala Gln Met Lys
        355                 360                 365 att gtg gac cct gaa acc ggt gtc act ctc cct cga aac caa ccc gga     1211
Ile Val Asp Pro Glu Thr Gly Val Thr Leu Pro Arg Asn Gln Pro Gly
        370                 375                 380 gag att tgc att aga gga gac caa atc atg aaa ggt tat ctt aat gat     1259
Glu Ile Cys Ile Arg Gly Asp Gln Ile Met Lys Gly Tyr Leu Asn Asp
385                 390                 395                 400 cct gag gcg acg gag aga acc ata gac aag gaa ggt tgg tta cac aca     1307
Pro Glu Ala Thr Glu Arg Thr Ile Asp Lys Glu Gly Trp Leu His Thr
                405                 410                 415 ggt gat gtg ggc tac atc gac gat gac act gag ctc ttc att gtt gat     1355
Gly Asp Val Gly Tyr Ile Asp Asp Asp Thr Glu Leu Phe Ile Val Asp
            420                 425                 430 cgg ttg aag gaa ctg atc aaa tac aaa ggg ttt cag gtg gca ccc gct     1403
Arg Leu Lys Glu Leu Ile Lys Tyr Lys Gly Phe Gln Val Ala Pro Ala
        435                 440                 445 gag ctt gag gcc atg ctc ctc aac cat ccc aac atc tct gat gct gcc     1451
Glu Leu Glu Ala Met Leu Leu Asn His Pro Asn Ile Ser Asp Ala Ala
        450                 455                 460 gtc gtc cca atg aaa gac gat gaa gct gga gag ctc cct gtg gcg ttt     1499
Val Val Pro Met Lys Asp Asp Glu Ala Gly Glu Leu Pro Val Ala Phe
465                 470                 475                 480 gtt gta aga tca gat ggt tct cag ata tcc gag gct gaa atc agg caa     1547
Val Val Arg Ser Asp Gly Ser Gln Ile Ser Glu Ala Glu Ile Arg Gln
                485                 490                 495 tac atc gca aaa cag gtg gtt ttt tat aaa aga ata cat cgc gta ttt     1595
Tyr Ile Ala Lys Gln Val Val Phe Tyr Lys Arg Ile His Arg Val Phe
            500                 505                 510 ttc gtc gaa gcc att cct aaa gcg ccc tct ggc aaa atc ttg cgg aag     1643
Phe Val Glu Ala Ile Pro Lys Ala Pro Ser Gly Lys Ile Leu Arg Lys
        515                 520                 525 gac ctg aga gcc aaa ttg gcg tct ggt ctt ccc aat taattctcat          1689
Asp Leu Arg Ala Lys Leu Ala Ser Gly Leu Pro Asn
        530                 535                 540 tcgctaccct cctttctctt atcatacgcc aacacgaacg aagaggctca attaaacgct   1749
gctcattcga agcggctcaa ttaaagctgc tcattcatgt ccaccgagtg ggcagcctgt   1809
cttgttggga tgttcttca tttgattcag ctgtgagaag ccagaccctc attatttatt   1869
gtgaaattca caagaatgtc tgtaaatcga tgttgtgagt gatgggtttc aaaacacttt   1929
```

```
tgacattgtt tacgttgtat ttcctgctgt tgaaaataac tactttgtat gacttttatt    1989
tgggaagata acctttcaaa aaaaaaaaaa aaaaaa                              2025
```

<210> SEQ ID NO 8
<211> LENGTH: 540
<212> TYPE: PRT
<213> ORGANISM: Liquidambar styraciflua

<400> SEQUENCE: 8

```
Met Glu Thr Gln Thr Lys Gln Glu Ile Ile Tyr Arg Ser Lys Leu
 1               5                  10                  15

Pro Asp Ile Tyr Ile Pro Lys His Leu Pro Leu His Ser Tyr Cys Phe
                20                  25                  30

Glu Asn Ile Ser Gln Phe Gly Ser Arg Pro Cys Leu Ile Asn Gly Ala
            35                  40                  45

Thr Gly Lys Tyr Tyr Thr Tyr Ala Glu Val Glu Leu Ile Ala Arg Lys
        50                  55                  60

Val Ala Ser Gly Leu Asn Lys Leu Gly Val Arg Gln Gly Asp Ile Ile
 65                  70                  75                  80

Met Leu Leu Leu Pro Asn Ser Pro Glu Phe Val Phe Ser Ile Leu Gly
                85                  90                  95

Ala Ser Tyr Arg Gly Ala Ala Ala Thr Ala Ala Asn Pro Phe Tyr Thr
            100                 105                 110

Pro Ala Glu Ile Arg Lys Gln Ala Lys Thr Ser Asn Ala Arg Leu Ile
        115                 120                 125

Ile Thr His Ala Cys Tyr Tyr Glu Lys Val Lys Asp Leu Val Glu Glu
    130                 135                 140

Asn Val Ala Lys Ile Ile Cys Ile Asp Ser Pro Asp Gly Cys Leu
145                 150                 155                 160

His Phe Ser Glu Leu Ser Glu Ala Asp Glu Asn Asp Met Pro Asn Val
                165                 170                 175

Glu Ile Asp Pro Asp Asp Val Val Ala Leu Pro Tyr Ser Ser Gly Thr
            180                 185                 190

Thr Gly Leu Pro Lys Gly Val Met Leu Thr His Lys Gly Gln Val Thr
        195                 200                 205

Ser Val Ala Gln Gln Val Asp Gly Glu Asn Pro Asn Leu Tyr Ile His
    210                 215                 220

Ser Glu Asp Val Val Leu Cys Val Leu Pro Leu Phe His Ile Tyr Ser
225                 230                 235                 240

Met Asn Val Met Phe Cys Gly Leu Arg Val Gly Ala Ala Ile Leu Ile
                245                 250                 255

Met Gln Lys Phe Glu Ile Tyr Gly Leu Leu Glu Leu Val Arg Ser Thr
            260                 265                 270

Gly Asp His His Ala Tyr Arg Thr Pro Ile Val Leu Ala Ile Ser Lys
        275                 280                 285

Thr Pro Asp Leu His Asn Tyr Asp Val Ser Ser Ile Arg Thr Val Met
    290                 295                 300

Ser Gly Ala Ala Pro Leu Gly Lys Glu Leu Glu Asp Ser Val Arg Ala
305                 310                 315                 320

Lys Phe Pro Thr Ala Lys Leu Gly Gln Gly Tyr Gly Met Thr Glu Ala
                325                 330                 335

Gly Pro Val Leu Ala Met Cys Leu Ala Phe Ala Lys Glu Gly Phe Glu
            340                 345                 350
```

```
Ile Lys Ser Gly Ala Ser Gly Thr Val Leu Arg Asn Ala Gln Met Lys
        355                 360                 365

Ile Val Asp Pro Glu Thr Gly Val Thr Leu Pro Arg Asn Gln Pro Gly
        370                 375                 380

Glu Ile Cys Ile Arg Gly Asp Gln Ile Met Lys Gly Tyr Leu Asn Asp
385                 390                 395                 400

Pro Glu Ala Thr Glu Arg Thr Ile Asp Lys Glu Gly Trp Leu His Thr
                405                 410                 415

Gly Asp Val Gly Tyr Ile Asp Asp Thr Glu Leu Phe Ile Val Asp
                420                 425                 430

Arg Leu Lys Glu Leu Ile Lys Tyr Lys Gly Phe Gln Val Ala Pro Ala
        435                 440                 445

Glu Leu Glu Ala Met Leu Leu Asn His Pro Asn Ile Ser Asp Ala Ala
        450                 455                 460

Val Val Pro Met Lys Asp Asp Glu Ala Gly Glu Leu Pro Val Ala Phe
465                 470                 475                 480

Val Val Arg Ser Asp Gly Ser Gln Ile Ser Glu Ala Glu Ile Arg Gln
                485                 490                 495

Tyr Ile Ala Lys Gln Val Val Phe Tyr Lys Arg Ile His Arg Val Phe
                500                 505                 510

Phe Val Glu Ala Ile Pro Lys Ala Pro Ser Gly Lys Ile Leu Arg Lys
        515                 520                 525

Asp Leu Arg Ala Lys Leu Ala Ser Gly Leu Pro Asn
        530                 535                 540

<210> SEQ ID NO 9
<211> LENGTH: 1544
<212> TYPE: DNA
<213> ORGANISM: Pinus taeda

<400> SEQUENCE: 9
```

| | | | | | |
|---|---|---|---|---|---|
| aaagataata | tatgtgtatg | cctactacta | cacattgttt | tgaagtgtgt | aaacatagtg | 60 |
| caacactagg | aggactcaca | atgagcactt | gttgacatga | actagctaa | atgcccaaca | 120 |
| atattagtga | aagctagtta | aactaacccc | tttgactttc | aagatgatat | atttatatcc | 180 |
| ctactacgtc | ttcctctttt | tgtctttctc | ttgtgattaa | accttccttg | aaacaattct | 240 |
| caaatgtaaa | attaaacctt | gaaacttgta | gagaccaaac | ttccctagga | gaaaccacat | 300 |
| ttatgacaac | atatatacac | caacccattg | catactataa | tattggaatt | acctgcagcg | 360 |
| aacgaaagaa | acgctgtctc | accaactcgt | gcactacatc | ccgaaactta | accttcccct | 420 |
| gatacagatt | gaagagccga | aaaaagcgtg | catccaaatt | tctggtatgg | tgaggagccg | 480 |
| aaaaacgcgt | gcgcctaatt | tttttgagat | gggccggaaa | ataatgcgtg | catctaaatt | 540 |
| ttcacgtgtc | gcgtattggc | gaggttgcgc | tgaatgtgat | cctgtgcgtg | agccacattc | 600 |
| attccattgg | ttgacccgcc | ggtaccgcga | ggaccgtggg | gtctcacaga | tacgcggatg | 660 |
| gtggatcagc | actgagaaga | ttagatgatg | accaggcggg | catttgaagt | aaaaacttgg | 720 |
| gggtggttgg | caagtacgcg | acaaagaggg | gtagtgcgca | aggaagcgag | ttggatgcaa | 780 |
| ataatattac | aaagtgggtt | ggtgggcatg | agcatcaacc | agaatgatgt | tgttgctggt | 840 |
| tccgtgcaaa | ttctgaccag | tagtttgaac | aatactaccc | aacttgtttt | tggtaaaaca | 900 |
| tgaagtgggt | aaggagaatt | gaacttacgt | ctcatggtaa | agggcaaggg | caaatgactt | 960 |
| aacacatacc | tttaactaat | aaaaatacccc | ctaacaaata | cgaaaacgaa | tgagttatca | 1020 |
| cagaccttca | actaataaga | tagccatcag | acccacatct | cctgactgac | caaaaacaaa | 1080 |

```
tgacttcaac caactaagat acccatcaaa gctaacccac aacccaattc ctcacttccc    1140
cttaccagac caaccaagca gacctacgcc attaactact ttaggacgtg ggaattgggg    1200
gtgccaccgt tgaagaatgg cactcagggt tggtaatccc tccacgtgta tgtagcagtc    1260
gtttggtgga gacggcgtgt ttgaatgtcc accttccagt ttggagaaca aggaaattgg    1320
gcttatatta ggcctggatc tcttgtttca gagcaggagt agttcaggac aggaactagc    1380
attcaagaat tcaattgccc tgccctgctc tgctctgctt tgctcaactt attgatccct    1440
gctctggttt gttcaatttc ttgaccectg ctgggttctg ctctggtttg cacactttct    1500
cgattatata agtcattttg gatccttgca aggaagagaa tatg                    1544

<210> SEQ ID NO 10
<211> LENGTH: 659
<212> TYPE: DNA
<213> ORGANISM: Pinus taeda

<400> SEQUENCE: 10
aaacaccaat ttaatgggat ttcagatttg tatcccatgc tattggctaa ggcattttc      60 ttattgtaat ctaaccaatt ctaatttcca ccctggtgtg aactgactga caaatgcggt    120
ccgaaaacag cgaatgaaat gtctgggtga tcggtcaaac aagcggtggg cgagagagcg    180
cgggtgttgg cctagccggg atgggggtag gtagacggcg tattaccggc gagttgtccg    240
aatggagttt tcggggtagg tagtaacgta gacgtcaatg gaaaaagtca taatctccgt    300
caaaaatcca accgctcctt cacatcgcag agttggtggc cacgggaccc tccacccact    360
cactcaatcg atcgcctgcc gtggttgccc attattcaac catacgccac ttgactcttc    420
accaacaatt ccaggccggc tttctataca atgtactgca caggaaaatc caatataaaa    480
agccggcctc tgcttccttc tcagtagccc ccagctcatt caattcttcc cactgcaggc    540
tacatttgtc agacacgttt tccgccattt ttcgcctgtt tctgcggaga atttgatcag    600
gttcggattg ggattgaatc aattgaaagg ttttatttt cagtatttcg atcgccatg      659

<210> SEQ ID NO 11
<211> LENGTH: 2251
<212> TYPE: DNA
<213> ORGANISM: Pinus taeda

<400> SEQUENCE: 11
ggccgggtgg tgacattat tcataaattc atctcaaaac aagaaggatt tacaaaaata      60
aaagaaaaca aaattttcat ctttaacata attataattg tgttcacaaa attcaaactt    120
aaacccttaa tataaagaat ttcttcaac aatacacttt aatcacaact tcttcaatca    180
caacctcctc caacaaaatt aaaatagatt aataaataaa taaacttaac tatttaaaaa    240
aaaatattat acaaaattta ttaaaacttc aaaataaaca actttttat acaaaattca    300 tcaaaacttt aaaataaagc taaacactga aaatgtgagt acatttaaaa ggacgctgat    360
cacaaaaatt ttgaaaacat aaacaaactt gaaactctac cttttaagaa tgagtttgtc    420
gtctcattaa ctcattagtt ttatagttcg aatccaatta acgtatcttt tattttatgg    480
aataagggtg ttttaataag tgattttggg atttttttag taatttattt gtgatatgtt    540 atggagttt taaaaatata tatatatata tatattttg ggttgagttt acttaaaatt    600
tggaaaaggt tggtaagaac tataaattga gttgtgaatg agtgttttat ggattttta    660 agatgttaaa tttatatatg taattaaaat tttattttga ataacaaaaa ttataattgg    720
```

```
ataaaaaatt gttttgttaa atttagagta aaaatttcaa aatctaaaat aattaaacac    780
tattattttt aaaaaatttg ttggtaaatt ttatcttata tttaagttaa aatttagaaa    840
aaattaattt taaattaata aacttttgaa gtcaaatatt ccaaatattt tccaaaatat    900
taaatctatt ttgcattcaa aatacaattt aaataataaa acttcatgga atagattaac    960
caatttgtat aaaaaccaaa aatctcaaat aaaatttaaa ttacaaaaca ttatcaacat   1020
tatgatttca agaaagacaa taaccagttt ccaataaaat aaaaaacctc atggcccgta   1080
attaagatct cattaattaa ttcttatttt ttaattttt tacatagaaa atatctttat   1140
attgtatcca agaaatatag aatgttctcg tccagggact attaatctcc aaacaagttt   1200
caaaatcatt acattaaagc tcatcatgtc atttgtggat tggaaattat attgtataag   1260
agaaatatag aatgttctcg tctagggact attaatttcc aaacaatttt caaaatcatt   1320
acattaaagc tcatcatgtc atttgtggat tggaaattag acaaaaaaaa tcccaaatat   1380
ttctctcaat ctcccaaaat atagttcgaa ctccatattt ttggaaattg agaattttt    1440
tacccaataa tatatttttt tatacatttt agagattttc cagacatatt tgctctggga   1500
tttattggaa tgaaggttga gttataaact ttcagtaatc caagtatctt cggttttga    1560
agatactaaa tccattatat aataaaaaca cattttaaac accaatttaa tgggatttca   1620
gatttgtatc ccatgctatt ggctaaggca tttttcttat tgtaatctaa ccaattctaa   1680
tttccaccct ggtgtgaact gactgacaaa tgcggtccga aaacagcgaa tgaaatgtct   1740
gggtgatcgg tcaaacaagc ggtgggcgag agagcgcggg tgttggccta gccgggatgg   1800
gggtaggtag acggcgtatt accggcgagt tgtccgaatg gagttttcgg ggtaggtagt   1860
aacgtagacg tcaatggaaa aagtcataat ctccgtcaaa aatccaaccg ctccttcaca   1920
tcgcagagtt ggtggccacg ggaccctcca cccactcact cgatcgcctg ccgtggttgc   1980
ccattattca accatacgcc acttgactct tcaccaacaa ttccaggccg gctttctata   2040
caatgtactg cacaggaaaa tccaatataa aaagccggcc tctgcttcct tctcagtagc   2100
ccccagctca ttcaattctt cccactgcag gctacatttg tcagacacgt tttccgccat   2160
ttttcgcctg tttctgcgga gaatttgatc aggttcggat tgggattgaa tcaattgaaa   2220
ggttttatt ttcagtattt cgatcgccat g                                   2251
```